US008293716B2

(12) United States Patent
Fishelson et al.

(10) Patent No.: US 8,293,716 B2
(45) Date of Patent: Oct. 23, 2012

(54) METHOD OF TREATING CANCER BY MODULATION OF MORTALIN

(75) Inventors: Zvi Fishelson, Tel-Aviv (IL); David Pilzer, Holon (IL)

(73) Assignee: Ramot At Tel Aviv University Ltd., Tel-Aviv (IL)

(*) Notice: Subject to any disclaimer, the term of this patent is extended or adjusted under 35 U.S.C. 154(b) by 0 days.

(21) Appl. No.: 11/440,132

(22) Filed: May 25, 2006

(65) Prior Publication Data
US 2006/0270622 A1   Nov. 30, 2006

Related U.S. Application Data

(60) Provisional application No. 60/684,538, filed on May 26, 2005.

(51) Int. Cl.
| | |
|---|---|
| C12N 15/11 | (2006.01) |
| G01N 33/53 | (2006.01) |
| A61K 39/395 | (2006.01) |
| A61K 45/00 | (2006.01) |
| C07H 21/04 | (2006.01) |

(52) U.S. Cl. .............. 514/44 A; 536/24.5; 530/387.2; 424/130.1; 424/278.1; 436/512

(58) Field of Classification Search ............ 514/44; 435/7.32; 536/23.1, 24.5; 424/93.21
See application file for complete search history.

(56) References Cited

U.S. PATENT DOCUMENTS

| | | | |
|---|---|---|---|
| 5,627,039 A * | 5/1997 | Pereira-Smith et al. ..... 435/7.23 |
| 5,670,530 A | 9/1997 | Chen et al. | |
| 2001/0018041 A1* | 8/2001 | Hanna et al. ................. 424/1.49 |
| 2003/0228294 A1* | 12/2003 | Dang et al. ................. 424/93.21 |
| 2005/0112130 A1* | 5/2005 | Bhat et al. .................. 424/155.1 |
| 2005/0164231 A1* | 7/2005 | Staudt et al. ..................... 435/6 |
| 2005/0281815 A1* | 12/2005 | Eshel et al. ................. 424/144.1 |

FOREIGN PATENT DOCUMENTS

| | | |
|---|---|---|
| EP | 0527494 | 2/1993 |
| WO | WO 01/80884 | 11/2001 |
| WO | WO 02/12194 | 2/2002 |
| WO | WO 2004/072027 | 8/2004 |
| WO | WO 2006/022344 | 2/2006 |
| WO | 2008/032324 A2 | 3/2008 |
| WO | 2008156012 A1 | 12/2008 |
| WO | 2009/040819 A2 | 4/2009 |

OTHER PUBLICATIONS

GR Devi, siRNA-based approaches in cancer therapy, 2006, Cancer Gene Therapy, vol. 13, pp. 819-829.*
Takeshita et al., Therapeutic potential of RNA interference against cancer, Aug. 2006, Cancer Science, vol. 97, pp. 689-696.*
Charlie Schmidt, Negotiating the RNAi patent thicket, Mar. 2007, Nature Biotechnology, vol. 25, pp. 273-275.*
Vickers et al., Efficient reduction of target RNAs by small interfering RNA and RNase-H-dependent antisense agents, Feb. 2003, The Journal of Biological Chemistry, vol. 278, pp. 7108-7118.*
Nancy D. Doolittle, State of the science in brain tumor classification, 2004, Seminars in Oncology Nursing, vol. 20, pp. 224-230.*
Dundas et al., Mortalin is over-expressed by colorectal adenocarcinomas and correlated with poor survival, 2005, Journal of Pathology, vol. 205, pp. 74-81.*
Takano et al., Elevated levels of mortalin expression in human brain tumors, 1997, Experimental Cell Research, vol. 237, pp. 38-45.*
Jurianz et al., K562 erythroleukemic cells are equipped with multiple mechanisms of resistance to lysis by complement, 2001, International Journal of Cancer, vol. 93, pp. 848-854.*
Chanan-Kahn et al., Bcl-2 antisense therapy in B-cell malignant proliferative disorders, 2004, Current Treatment Options in Oncology, vol. 5, pp. 261-267.*
Bohana-Kashtan et al. "Cell Signals Transduced by Complement", Molecular Immunology, 41: 583-597, 2004.
Britten et al. "A Phase I and Pharmacokinetic Study of the Mitochondrial-Specific Rhodacyanine Dye Analog MKT 077", Clinical Cancer Research, 6: 42-49, 2000.
Carette et al. "Implication of PbP74/Mortalin/GRP75 in the Radio-Adaptive Response", International Journal of Radiation Biology, 78(3): 183-190, 2002.
Carney et al. "Elimination of Terminal Complement Intermediates From the Plasma Membrane of Nucleated Cells: The Rate of Disappearance Differs for Cells Carrying C5b-7 or C5b-8 or a Mixture of C5b-8 With a Limited Number of C5b-9", The Journal of Immunology, 134( 3): 1804-1809, 1985.
Carney et al. "Elimination of Terminal Complement Compleies in the Plasma Membrane of Nucleated Cells: Influence of Extracellular Ca2+ and Association With Cellular Ca2+", The Journal of Immunology, 137(1): 263-270, 1986.
Cragg et al. "Complement Mediated Cell Death is Associated With DNA Fragmentation", Cell Death and Differentiation, 7: 48-58, 2000.
Dashiell et al. "Terminal Complement Complexes Concomitantly Stimulate Proliferation and Rescue of Schwann Cells From Apoptosis", GLIA, 30(2): 187-198, 2000.
Dundas et al. "Mortalin is Over-Expressed by Colorectal Adenocarcinomas and Correlates With Poor Survival", Journal of Pathology, 205: 74-81, 2005. Fishelson et al. "Contribution of Heat Shock Proteins to Cell Protection From Complement-Mediated Lysis", International Immunology, 13(8): 983-991, 2001.
Fishelson et al. "Obstacles to Cancer Immunotherapy: Expression of Membrane Complement Regulatory Proteins (mCRPs) in Tumors", Molecular Immunology, 40: 109-123, 2003.
Gelderman et al. "The Inhibitory Effect of CD46, CD55, and CD59 on Complement Activation After Immunotherapeutic Treatment of Cervical Carcinoma Cells With Monoclonal Antibodies or Bispecific Monoclonal Antibodies", Laboratory Investigation, 82(4): 483-493, 2002.
Gelderman et al. "Tumor-Specific Inhibition of Membrane-Bound Complement Regulatory Protein Crry With Bispecific Monoclonal Antibodies Prevents Outgrowth in a Rat Colorectal Cancer Lung Metastases Model", Cancer Research, 64: 43004372, 2004.
Gralinski et al. "Heat Stress Protects the Perfused Rabbit Heart From Complement-Mediated Injury", AJP—Heart and Circulatory Physiology, 271(2): H571-H578, 1996. Abstract.

(Continued)

*Primary Examiner* — Dana Shin
(74) *Attorney, Agent, or Firm* — Browdy and Neimark, PLLC

(57) ABSTRACT

A method of treating cancer in a subject in need thereof is disclosed. The method comprises administering to the subject a siRNA molecule capable of inducing degradation of an mRNA encoding a polypeptide of SEQ ID NO: 1 in cells of the cancer thereby treating the cancer in the subject.

4 Claims, 8 Drawing Sheets

OTHER PUBLICATIONS

Harris et al. "Tumour Cell Killing Using Chemically Engineered Antibody Constructs Specific for Tumour Cells and the Complement Inhibitor CD59", Clinical and Experimental Immunology, 107: 364-371, 1997.

Johannesen et al. "Is Mortalin A Candidate Gene for TIDM?", Autoimmunity, 37(6/7): 423-430, 2004. Harris et al. "Tumour Cell Killing Using Chemically Engineered Antibody Constructs Specific for Tumour Cells and the Complement Inhibitor CD59", Clinical and Experimental Immunology, 107: 364-371, 1997.

Johannesen et al. "Is Mortalin A Candidate Gene for TIDM?", Autoimmunity, 37(6/7): 423-430, 2004.

Kaul et al. "Overexpressed Mortalin (Mot-2)/Mthsp70/GRP75 and hTERT Cooperate to Extend the in Vivo Lifespan of Human Fibroblasts", Experimental Cell Research, 286: 96-101, 2003.

Kirmanoglou et al. "Expression of Mortalin in Patients With Chronic Atrial Fibrillation", Basic Research in Cardiology, 99: 404-408, 2004.

Koski et al. "Cytolysis of Nucleated Cells by Complement: Cell Death Displays Multi-Hit Characteristics", Proc. Natl. Acad. Sci. USA, 80: 3816-3820, 1983.

Morgan et al. "Complement Lysis of U937, A Nucleated Mammalian Cell Line in the Abesence of C9: Effect of C9 on C5b-8 Mediated Cell Lysis", The Journal of Immunology, 136(9): 3402-3406, 1986.

Morgan et al. "Recovery of Human Neutrophils From Complement Attack: Removal of the Membrane Attack Complex by Endocytosis and Exocytosis", The Journal of immunology, 138(1): 246-253, 1987.

Propper et al. "Phase I Trial of the Selective Mitochondrial Toxin MKT 077 in Chemo-Resistant Solid Tumours", Annals of Oncology, 10: 923-927, 1999.

Ran et al. "Extramitochondrial Localization of Mortalin/Mthsp70/PBP74/GRP75", Biochemical and Biophysical Research Communications, 275: 174-179, 2000.

Reiter et al. "Sublytic Complement Attack Protects Tumor Cells From Lytic Doses of Antibody and Complement", European Journal of Immunology, 22(5): 1207-1213, 1992. Abstract.

Scolding et al. "Vesicular Removal by Oligodendrocytes of Membrane Attack Complexes Formed by Activated Complement", Nature, 339: 620-622, 1989.

Shin et al. "Global Profiling of the Cell Surface Proteome of Cancer Cells Uncovers an Abundance of Proteins With Chaperone Function", The Journal of Biological Chemistry, 278(9): 7607-7616, 2003.

Sims et al. "Repolarization of the Membrane Potential of Blood Platelets After Complement Damage: Evidence for a Ca++ -Dependent Exocytotic Elimination of C5b-9 Pores", Blood, 68(2): 556-561, 1986.

Stein et al. "Ectocytosis Caused by Sublytic Autologous Complement Attack on Human Neutrophils", Biochemical Journal, 274: 381-386, 1991.

Takano et al. "Elevated Levels of Mortalin Expression in Human Brain Tumors", Experimental Cell Research, 237: 38-45, 1997.

Takashima et al. "Proteomic Profiling of Heat Shock Protein 70 Family Members as Biomarkers for Hepatitis C Virus-Related Hepatocellular Carcinoma", Proteomics, 3: 2487-2493, 2003.

VanBuskirk et al. "Cellular and Subcellular Distribution of PBP72/74, A Peptide-Binding Protein That Plays a Role in Antigen Processing", The Journal of Immunology, 146(2): 500-506, 1991.

Voisine et al. "The Protein Import Motor of Mitochondria: Unfolding and Trapping of Preproteins Are Distinct and Separable Functions of Matrix Hsp70", Cell, 97: 565-574, 1999.

Wadhwa et al. "Cellular Mortality to Immortalization: Mortalin", Cell Structure and Function, 19(1): 1-10, 1994.

Wadhwa et al. "Selective Toxicity of MKT-077 to Cancer Cells is Mediated by Its Binding to the Hsp70 Family Protein Mot-2 and Reactivation of P53 Function", Cancer Research, 60: 6818-6821, 2000.

Wadhwa et al. "Rhodacyanine Dye MKT-077 Inhibits in Vitro Telomerase Assay But Has No Detectable Effects on Telomerase Activity in Vivo", Cancer Research, 62: 4434-4438, 2002.

Wadhwa et al. "An Hsp70 Family Chaperone, Mortalin/Mthsp70/PBP74/Grp75: What, When, and Where?", Cell Stress & Chaperones, 7(3): 309-316, 2002.

Wadhwa et al. "Mortalin: A Potential Candidate for Biotechnology and Biomedicine", Histology and Histopathology, 17(4): 1173-1177, 2002. Abstract.

Wadhwa et al. "Targeting Mortalin Using Conventional and RNA Helicase-Coupled Hammerhead Ribozymes", EMBO Reports, 4(6): 596-601, 2003.

Wadhwa et al. "Reduction in Mortalin Level by its Antisense Expression Causes Senescence-Like Growth Arrest in Human Immortalized Cells", The Journal of Gene Medicine, 6(4): 439-444, 2004.

Walport "Complement", New England Journal of Medicine, 344(14): 1058-1066, 2001.

Deocaris et al. "Mortalin Sensitizes Human Cancer Cells to MKT-077-Induced Senescence", Cancer Letters, 11 P., 2007.

Mansoor et al. "Potentiation of the Antiproliferative Activity of MKT-077 by Loperamide, Diltiazem and Tamoxifen", Oncology Reports 2003, 10(6): 2023-2026, 2003, Database Medline [Online], US National Library of Medicine (NLM), Database Accession No. NLM14534737. Abstract.

Modica-Napolitano et al. "The Selective in Vitro Cytotoxicity of Carcinoma Cells by AZT is Enhanced by Concurrent Treatment With Delocalized Lipophilic Cations", Cancer Letters, 198(1): 59-68, 2003. Abstract, Figs.3, 4, Introduction, p. 59, 60, p. 66, 1st Col., Last §, p. 67, 1st §.

Pilzer et al. "Mortalin/GRP75 Promotes Release of Membrane Vesicles From Immune Attacked Cells and Protection From Complement-Mediated Lysis", International Immunology, 17(9): 1239-1248, 2005. Abstract.

International Search Report Dated Mar. 28, 2008 From the International Searching Authority Re.: Application No. PCT/IL2007/001132.

Written Opinion Dated Mar. 28, 2008 From the International Searching Authority Re.: Application No. PCT/IL2007/001132.

Response Dated Sep. 26, 2007 to Official Action of Mar. 28, 2007 From the US Patent and Trademark Office Re.: U.S. Appl. No. 11/440,132.

International Search Report Dated Mar. 25, 2009 From the International Search Authority Re.: Application No. PCT/IL2008/001295.

Written Opinion Dated Mar. 25, 2009 From the International Searching Authority Re.: Application No. PCT/IL2008/001295.

Ohtsuka et al., "Mortalin is a Novel Mediator of Erythropoietin Signaling", European Journal of Haematology, XP002519032, 79(2): 114-125 (2007).

Bhattacharyya et al., "Cloning and Subcellular Localization of Human Mitochondrial hsp70" J. Biol. Chem., 270:1705-1710 (1995).

Bindon et al., "Human Monoclonal IgG Isotypes Differ in Complement Activating Function at the Level of C4 as Well as C1q," J. Exp. Med. 168:127-142 (1988).

Curtis MA.,"New monoclonal antibodies for hematologic malignancies (and breast cancer)." Med Health R. I. 86:256-7 (2003).

Gadjeva et al, "Interaction of Human C1q with IgG and IgM: Revisited" Biochemistry 47:13093-13102 (2008).

Harris., "Monoclonal Antibodies as Therapeutic Agents for Cancer," Lancet Oncol. 5:292-302 (2004).

Houshmand P, Zlotnik A., "Targeting Tumor Cells." Curr Opin Cell Biol. 15:640-6 (2003).

Kregel, et al. "Molecular Biology of Thermoregulation Invited Review: Heat shock proteins: modifying factors in physiological stress responses and acquired thermotolerance," J Appl Physiol 92:2177-2186 (2002).

Rudiger et al.,"Modulation of substrate specificity of the DnaK chaperone by alteration of a hydrophobic arch" J. Mol. Biol. 304: 245-251 (2000).

Tavaria, et al., "A Hitchhiker's Guide to the Human Hsp70 Family," Cell Stress & Chaperones 1:23 (2006).

Lucisano Valim and Lachmann, "The effect of antibody isotype and antigenic epitope density on the complement-fixing activity of immune complexes: a systematic study using chimaeric anti-NIP antibodies with human Fc regions" Clin. Exp. Immunol. 84:1-8(1991).

Wadhwa, et al., "Upregulation of mortalin/mthsp70/Grp75 contributes to human carcinogenesis," Int J Cancer 118:2973-2980 (2006).
Zhou, et al., "The role of complement and the mechanism of action of Rituximab for B-cell lymphoma: implications for therapy" The Oncologist 13:954-966 (2008).
International Preliminary Examination Report on Patentability and Written Opinion, for PCT/IL2008/001295, Issued Mar. 30, 2010.
Bernstein et al. "Role for a bidentate ribonuclease in the initiation step of RNA interference" Nature, vol. 409:18, pp. 363-366 (2001).
Brantl "Review Antisense-RNA regulation and RNA interference" Biochimica et Biophysica Acta 1575:15-25 (2002).
Brinker et al. "Ligand Discrimination by TPR Domains: Relevance and Selectivity of EEVD-Recognition in Hsp70•hop•Hsp90 complexes" J. Biol Chem 277:19265-19275 (2002).
Cullen "RNA interference: antiviral defense and genetic tool" Nature Immunol. vol. 3, No. 7. pp. 597-599 (2002).
Hammond "Post-Transcriptional Gene Silencing by Double-Stranded RNA" Nat Rev Genet, 2:110-119 (2001).
Hutvágner et al. "RNAi: nature abhors a double-strand" Current Opinion Genetics & Development 12:225-232 (2002).
"Homo sapiens heat shock 70kDa protein 9B (mortalin-2) (HSPA9B), nuclear gene encoding mitochondrial protein, mRNA" NCBI Reference Sequence: NM_004134.3, Oct. 5, 2003.
"Homo sapiens heat shock 70kDa protein 9B (mortalin-2) (HSPA9), nuclear gene encoding mitochondrial protein, mRNA" NCBI Reference Sequence: NM_004134, Version NM_4134.6, Nov. 10, 2010.
"stress-70 protein, mitochondrial precursor [Homo sapiens]" NCBI Reference Sequence: NP_004125.3, Nov. 10, 2010.
Sadekova et al. "Induction of PBP74/mortalin/Grp75, a member of the hsp70 family, by low doses of ionizing radiation: a possible role in induced radioresistance" Int J Radiat Biol. 76(2):653-60 (1997) (Abstract only).
Sharp "RNA interference—2001" Genes Dev. 15: 485-490 (2001).
Pilzer et al. "Mortalin Inhibitors Sensitize K562 Leukemia Cells to Complement-Dependent Cytotoxicity", International Journal of Cancer, 126: 1428-1435 (2010).
Bernstein et al. "Role for a Bidentate Ribonuclease in the Initiation Step of RNA Interference", Nature, 409: 363-366, (2001).
Brantl "Antisense-RNA Regulation and RNA Interference", Biochimica et Biophysica Acta, 1575: 15-25 (2002).
Brinker et al. "Ligand Discrimination by TPR Domains. Relevance and Selectivity of EEVD-Recognition in Hsp70•Hop•Hsp90 Complexes", The Journal of Biological Chemistry, 277(22): 19265-19275 (2002).
Hammond et al. "Post-Transcriptional Gene Silencing by Double-Stranded RNA", Nature Reviews Genetics, 2: 110-111 (2001).
Hutvágner et al. "RNAi: Nature Abhors A Double-Strand", Current Opinion in Genetics & Development, 12: 225-232,) (2002).
Nucleotide "Homo sapiens Heat Shock 70kDa Protein 9 (Mortalin) (HSPA9), Nuclear Gene Encoding Mitochondrial.Protein, mRNA", Nucleotide Results, NCBI Reference Sequence: NM_004134.6, Accession No. NM_004134.(Nov. 10, 2010).
Nucleotide "Homo sapiens Heat Shock 70kDa Protein 9B (Mortalin-2) (HSPA9B), Nuclear Gene Encoding Mitochondrial Protein, mRNA", Nucleotide Results, NCBI Reference Sequence: NM_004134.3, Accession No. NM_004134. (Oct. 5, 2003).
Odunuga et al. "Tetratricopeptide Repeat Motif-Mediated Hsc70-mSTI1 Interaction", The Journal of Biological Chemistry, 278(9): 6896-6904 (2003).
Protein "Stress-70 Protein, Mitochondrial Precursor [Homo sapiens]", Protein Results, NCBI Reference Sequence: NP_004125.3, Accession No. NP_004125 (Nov. 10, 2010).

Sadekova et al. "Induction of PBP74/Mortalin/Grp75, A member of the Hsp70 Family, by Low Doses of Ionizing.Radiation: A Possible Role in Induced Radioresistance", International Journal of Radiation Biology, 72(6): 653-660 (1997) (Abstract).
Sharp "RNA Interference—2001", Genes & Development, 15: 485-490 (2001).
Tuschl "RNA Interference and Small Interfering RNAs", ChemBiochem, 2: 239-245 (2001).
Yaguchi et al. "Involvement of Mortalin in Cellular Senescence From the Perspective of its Mitochondrial Import, Chaperone, and Oxidative Stress Management Functions", Annals of the New York Academy of Sciences, 1100: 306-311 (2007).
International Preliminary Report on Patentability Dated Apr. 8, 2010 From the International Bureau of WIPO Re.: Application No. PCT/IL2008/001295.
Deocaris et al. "Mortalin Sensitizes Human Cancer Cells to MKT-077-Induced Senescence", Cancer Letters, XP025319755, 252(2): 259-269, p. 263, Fig.1 (2007).
Ran et al. "Extramitochondrial Localization of Mortalin/Mthsp70/PBP74/GRP75", Biochemical and Biophysical Research Communications, 275: 174-179 (2000).
Takashita et al. "Therapeutic Potential of RNA Interference Against Cancer", Cancer Science, 97(8): 689-696 (2006).
Aoudjit et al. "P38 Mitogen-Activated Protein Kinase Protects Glomerular Epithelial Cells from Complement-Mediated Cell Injury," AMJ Physiol Renal Physiol, 285:F765-F774 (2003).
Sreedhar et al., "Hsp90 Inhibition Accelerates Cell Lysis: Anti-hsp90 Ribozyme Reveals a Complex Mechanism of hsp90 Inhibitors Involving Both Superoxide- and hsp90-Dependent Events," J. Biol Chem. 278:35231-35240 (2003).
Lanneau et al., "Apoptosis versus cell differentiation: Role of Heat Shock Proteins hsp90, hsp70 and hsp27," Prion 1:53-60 (2007).
Lanneau at al., "Heat Shock Proteins: Cell Protection Through Protein Triage," The Scientific World Journal, 10:1543-1552 (2010).
Restriction Official Action Dated Jan. 31, 2012 From the US Patent and Trademark Office Re. U.S. Appl. No. 12/679,938.
Restriction Official Action Dated Dec. 19, 2011 From the US Patent and Trademark Office Re. U.S. Appl. No. 12/310,790.
Tatsuta et al. "Pharmacokinetic Analysis and Antitumor Efficacy of MKT-077, A Novel Antitumor Agent", Cancer Chemotherapy and Pharmacology, 43(4): 295-301, 1999.
Office Action Dated Mar. 23, 2012 From the US Patent and Trademark Office Re. U.S. Appl. No. 12/679,938.
Garrido et al. "Heat Shock Proteins 27 and 70. Anti-Apoptotic Proteins With Tumorigenic Properties", Cell Cycle, 5(22): 2592-2601, Nov. 15, 2006.
Tuschl "RNA Interference and Small Interfering RNAs" Chembiocchem vol. 2, pp. 239-245 (2001).
Odunga et al. "Tetratricopeptide Repeat Motif-mediated Hsc70-mSTI1 Interaction: Molecular Characterization of the Critical Contacts for Successful Bing and Specificity," J Biol Chem 278:6896-6904 (2003).
Yaguchi et al, "Involvement of Mortalin in Cellular Senescence from the Perspective of its Mitochondrial Import, Chaperone, and Oxidative Stress Management Functions," Ann. N.Y. Acad. Sci. 1100:306-311 (2007).
Carette et al., "Implication of PBP74/mortalin/GRP75 in the radio-adaptive response," Int J Radiat Biol, 78:183-190 (abstract only), published in Mar. 2002.

* cited by examiner peptide 1: DAGQISGLNVLR - SEQ ID NO: 4
peptide 2: VQQTVQDLFGR - SEQ ID NO: 5
peptide 3: QAVTNPNNTFYATK - SEQ ID NO: 6
peptide 4: NAVITVPAYFNDSQR - SEQ ID NO: 7
peptide 5: DIGEVILVGGMTR - SEQ ID NO: 8
peptide 6: TFDISILEIQKGVFE - SEQ ID NO: 9
peptide 7: QTQVEIKVCQGERE - SEQ ID NO: 10

Fig. 7
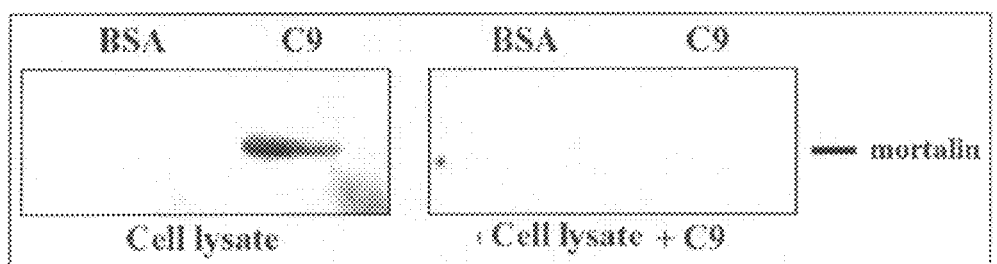
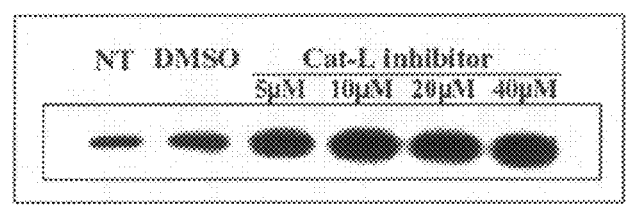
Fig. 8a
Fig. 8b
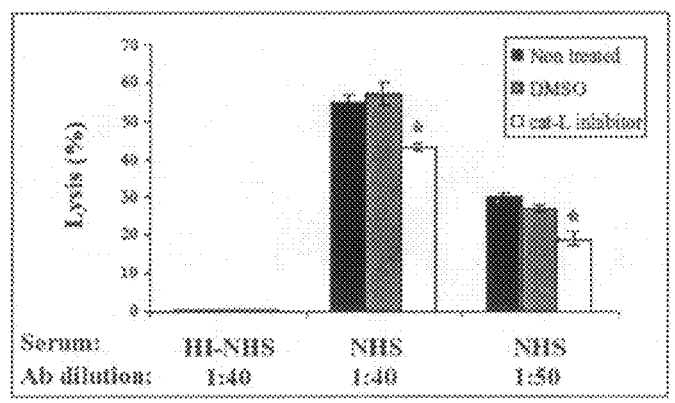
Fig. 9
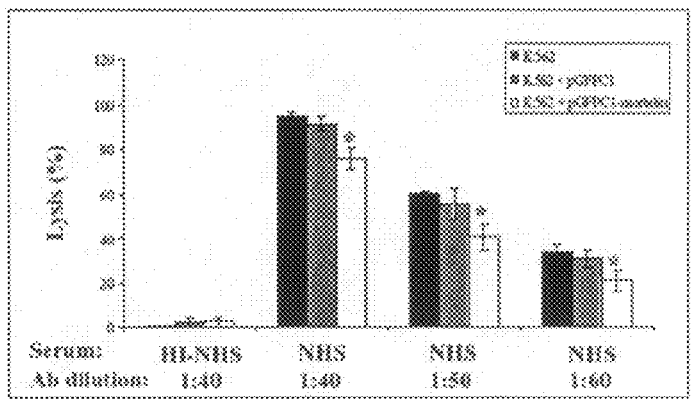

METHOD OF TREATING CANCER BY MODULATION OF MORTALIN

RELATED APPLICATION

This application claims the benefit of U.S. Provisional Patent Application No. 60/684,538 filed on May 26, 2005, the contents of which are incorporated herein by reference.

FIELD AND BACKGROUND OF THE INVENTION

The present invention relates to methods of modulating levels/activity of 70 kilodalton heat-shock protein (HSP70) family members, for regulating vesicular shedding of complement, for regulating complement-mediated cytotoxicity, and for treating diseases which are associated with pathological cells and are treatable via complement-mediated cytolysis of such cells, and/or which are associated with pathological complement-mediated cytolysis; and to articles of manufacture which comprise compounds for practicing such methods. The present invention more particularly relates to methods of decreasing levels/activity of mortalin for decreasing vesicular shedding of complement, for increasing complement-mediated cytolysis of pathological cells, and for treating diseases, such as tumoral, infectious, autoimmune and transplantation-related diseases, which are associated with such cells, and are treatable via complement-mediated cytolysis of, such cells, where such methods are effected using: substantially cell membrane-impermeable compounds; and/or compounds for decreasing levels/activity of mortalin in combination with compounds for increasing association of complement with pathological cells. The present invention further particularly relates to methods of increasing levels/activity of mortalin for decreasing vesicular shedding of complement, for decreasing pathological complement-mediated cytotoxicity, and for treating diseases associated with such pathological cytotoxicity, such as autoimmune, immune complex, and transplantation-related diseases; and to articles of manufacture which comprise compounds for practicing such methods.

Diseases such as tumoral, infectious, autoimmune and transplantation-related diseases, which are associated with pathological cells and are treatable via complement-mediated cytolysis of such cells represent numerous highly debilitating and/or lethal diseases for which no optimal therapy exists. Similarly, diseases associated with pathological complement-mediated cytotoxicity, such as autoimmune, immune-complex and transplantation-related diseases, also represent numerous highly debilitating and/or lethal diseases for which no optimal therapy exists. There is therefore a long-felt and urgent need in the art for novel and maximally effective methods and therapeutic agents for treating such diseases.

The complement system consists of more than twenty blood plasma proteins that cooperate with other sections of the innate and acquired immune systems in clearance of pathogenic organisms, immune complexes and apoptotic cells (Walport, M. J. 2001. N Engl J Med 344:1058). The complement activation cascade culminates in formation of the membrane attack complex (MAC), made of complement C5b, C6, C7, C8 and C9 proteins (termed "C5b-9"), and its insertion into the plasma membrane of target cells (Muller-Eberhard, H. J. 1986. Annu Rev Immunol 4:503). Membrane insertion begins when C5b-7 forms, is enhanced upon formation of C5b-8 complex and is maximal upon binding and oligomerization of C9 and formation of a transmembrane, cylinder-shape polyC9 complex attached to C5b-8. At supralytic doses, MAC normally functions to induce rapid cell death by necrosis (Koski, C. L. et al.,1983. Proc Natl Acad Sci U S A 80:3816) or apoptosis (Cragg, M. S. et al., 2000. Cell Death Differ 7:48). At low, sublytic doses, MAC acts as a potent stimulator of numerous cellular activities (for review see Bohana-Kashtan, O. et al., 2004. Mol Immunol 41:583). Treatment with sublytic MAC has been shown to transduce either anti-necrotic (Reiter, Y. et al., 1992. Eur J Immunol 22:1207) or anti-apoptotic (Dashiell, S. M. et al., 2000. Glia 30:187) signals into various cells.

As a means of protection from complement, nucleated cells can remove the MAC from their plasma membrane by endocytosis or vesiculation (Sims, P. J. and Wiedmer, T. 1986. Blood 68:556; Morgan, B. P. et al., 1987. J Immunol 138:246; Carney, D. F. et al., 1985. J Immunol 134:1804) or proteolytic fragmentation. Physical removal of MAC by vesiculation has been demonstrated in several cell types including neutrophils, oligodendrocytes and platelets, and in the tumor cell lines U937 and K562 (Sims, P. J. and Wiedmer, T. 1986. Blood 68:556; Scolding, N. J. et al., 1989. Nature 339:620; Morgan, B. P. et al., 1986. J Immunol 136:3402; Morgan, B. P. 1992. Curr Top Microbiol Immunol 178:115). The shed vesicles have a high content of cholesterol and diacylglycerol (Stein, J. M. and Luzio, J. P. 1991. Biochem J. 274 (Pt 2):381) and are loaded with MAC and C9, suggesting a selective sorting on the cell surface prior to shedding. To date, little is known about the molecular mechanism responsible for MAC vesiculation. Extracellular Ca2+ has been suggested to play a role in elimination of terminal complement complexes (Carney DF. et al., 1986. Elimination of terminal complement complexes in the plasma membrane of nucleated cells: influence of extracellular Ca2+ and association with cellular Ca2+. J Immunol. 137:263-70). Various proteins capable of regulating complement activity are known. In particular, three membrane complement regulatory proteins (mCRPs) inhibit complement activation: decay accelerating factor (DAF, CD55), membrane cofactor protein (MCP, CD46) and CD59.

Removal of complement from nucleated cells may be associated with disease pathogenesis. For example, MAC removal has been shown to protect cancer cells from complement-mediated cytotoxicity. Lysis of tumor cells by homologous complement is inefficient primarily due to their capacity to subvert complement binding and damage. In general, tumor cell protective mechanisms may be divided into intrinsic and induced mechanisms. Intrinsic mechanisms determine the basal resistance of the tumor cells to homologous complement, and the induced protective mechanisms represent the capacity of the tumor cell to react to various external stimuli (for example, cytokines, toxins, hormones as well as an ongoing complement activation) and to increase its level of protection from complement. Membrane complement regulatory proteins are over-expressed on the surface of cancer cells, and render them resistant to autologous complement (Fishelson Z. et al., 2003. Obstacles to cancer immunotherapy: expression of membrane complement regulatory proteins (mCRPs) in tumors. Mol Immunol. 40:109-23). Neutralization of mCRPs with blocking antibodies sensitizes both human leukemic and carcinoma cells to lysis by human complement. Thus, the capacity of cells to shed MAC so as to avoid cytotoxicity is problematic for disease treatment approaches involving antibody-mediated cytolysis of pathological cells. In recent years, new monoclonal antibodies have been designed to target and kill tumor cells. This era of targeted therapy has brought to the clinic a handful of monoclonal antibodies, including Rituxan (rituximab), designed for relapsed or refractory CD20-positive non-Hodgkin B-cell lymphoma, Herceptin (trastuzumab) for breast tumors overexpressing the human epidermal growth factor receptor 2 (HER-2) and others. While such disease treatments have only yielded partial benefits, there is nevertheless great interest in antibody-based therapeutics for hematopoietic malignant neoplasms and solid tumors, due to the inefficiency and harmful side-effects of conventional cancer treatment approaches which involve chemo- and radio-therapy. Various studies have investigated the role of complement-mediated lysis in antibody-mediated cancer therapy in an attempt to elucidate means of achieving therapeutic improvement via such treatment. By introducing human IgGI heavy and light chain domains, the antiproliferative properties of a precursor murine monoclonal anti-p185HER antibody to Herceptin were extended by its capacity to induce antibody-dependent cell-mediated cytotoxicity (ADCC). It has been shown that complement activation on various HER-2 positive tumor cell lines upon sensitization with the humanized anti-p185HER antibody leads to opsonization of the tumor cells with C3b. However, complement-mediated tumor cell lysis became only possible upon neutralization of mCRP. Part of the anti-tumor effect of rituximab has been ascribed to its capacity to bind C1q, activate complement and eventually kill the cells.

Targeting of proteins capable of regulating complement has been suggested for tumor therapy (Harris, C. et al., 1997. Tumour cell killing using chemically engineered antibody constructs specific for tumour cells and the complement inhibitor CD59. Clin Exp Immunol 107:364; Blok, V. T. et al., 1998. A bispecific monoclonal antibody directed against both the membrane-bound complement regulator CD55 and the renal tumor-associated antigen G250 enhances C3 deposition and tumor cell lysis by complement. J Immunol 160:3437; Gelderman, K. A. et al., 2002. The inhibitory effect of CD46, CD55, and CD59 on complement activation after immunotherapeutic treatment of cervical carcinoma cells with monoclonal antibodies or bispecific monoclonal antibodies. Lab Invest 82:483; Gelderman, K. A. et al., 2004. Tumor-specific inhibition of membrane-bound complement regulatory protein Crry with bispecific monoclonal antibodies prevents tumor outgrowth in a rat colorectal cancer lung metastases model. Cancer Res 64:4366.). One possible approach is the construction of bispecific monoclonal antibodies consisting of one Fab moiety directed to a tumor specific antigen and another directed to an mCRP. Tumor-directed bispecific antibodies with an anti-mCRP moiety would enable specific targeting of complement regulators on tumor cells without impairment of healthy tissue. Proof of concept that a bispecific antibody directed against an mCRP may be protective against malignant cells has been achieved in-vitro. Several forms of bispecific antibodies have been generated to link tumor cells more effectively to immune effector cells and some of them are already in clinical trials. For example, a phase II study showed that the bispecific antibody MDX-H210 (anti-HER2/anti-CD64) together with GM-CSF is therapeutically active against hormone refractory HER2+ prostate cancer.

Mechanisms protecting cells from heat-shock and from complement share some resemblance. For example, both of these shock responses depend on de-novo protein synthesis, exhibit similar functional kinetics, and studies have suggested a role for members of the 70 kilodalton heat shock protein (HSP70) family proteins in regulation of complement-mediated cytolysis (Fishelson Z. et al., 2001. Contribution of heat shock proteins to cell protection from complement-mediated lysis. Int Immunol. 13:983-991).

Mortalin, also known as GRP75, PBP74, mitochondrial HSP75 and mot-2, is a member of the HSP70 family (GeneCard #GC05M137967). This protein has been assigned multiple functions including stress response (Carette, J. et al., 2002. Int J Radiat Biol 78:183), glucose regulation, p53 inactivation, control of cell proliferation, differentiation, tumorigenesis and mitochondrial import (reviewed in Wadhwa, R. et al., 2002. Cell Stress Chaperones 7:309; Voisine, C. et al., 1999. Cell 97:565). Mortalin has been mainly described inside cells, in mitochondria and several other cytoplasmic locations such as endoplasmic reticulum and cytoplasmic vesicles (Ran, Q. et al., 2000. Biochem Biophys Res Commun 275:174). Mortalin is ubiquitously and constitutively expressed in normal tissues, and has been shown to be displayed on the surface of mouse B-cells and macrophages (VanBuskirk, A. M. et al., 1991. J Immunol 146:500). Its expression level is upregulated in some tumors, such as neuroblastoma, lung adenocarcinoma, leukemia and ovarian cancer cells (Takano, S. et al., 1997. Exp Cell Res 237:38; Dundas, SR. et al., 2004. J Pathol 205:74; Shin, B. K. et al., 2003. J Biol Chem 278:7607), as well as during infection and inflammation (Kirmanoglou, K. et al., 2004. Basic Res Cardiol 99:404; Johannesen, J. et al., 2004. Is mortalin a candidate gene for T1DM ? Autoimmunity 37:423). Overexpression of mortalin in normal cells considerably extends their lifespan (Kaul, S. C. et al., 2003. Exp Cell Res 286:96), while reduction of mortalin levels in immortalized cells causes growth arrest (Wadhwa, R. et al., 2004. J Gene Med 6:439; Wadhwa et al., 1994. Cellular mortality to immortalization: mortalin. Cell Struct Funct. 19:1-10). In view of the expression of mortalin in cancers, the use of this protein as therapeutic target has been proposed (Wadhwa R. et al., 2002. Mortalin: a potential candidate for biotechnology and biomedicine. Histol Histopathol. 17:1173-7).

Thus, in view of the possible role of HSP70 family proteins in mediating protection from complement-mediated cytotoxicity, and in view of the overexpression of such proteins in pathological cells susceptible to elimination via such cytotoxicity, suitable modulation of levels/activity of such proteins may represent a potentially optimal strategy for treating diseases associated with pathological complement-mediated cytotoxicity, and/or associated with pathological cells and treatable via complement-mediated cytolysis of such cells.

Several prior art approaches have been proposed involving decreasing levels/activity of HSP70 family proteins, such as mortalin, for treating diseases associated with pathological cells and treatable via complement-mediated cytolysis of such cells.

One approach involves administration of the mortalin inhibitor MKT-077 (formerly FJ-776) for treatment of cancers characterized by wild-type p53 (Wadhwa R. et al., 2000. Cancer Research 60, 6818-6821), chemo-resistant solid tumors (Propper D. J. et al., 1999. Phase I trial of the selective mitochondrial toxin MKT077 in chemo-resistant solid tumours. Ann. Oncol., 10: 923-927), untreatable/treatment-refractory solid tumors (Britten C. D. et al, 2000. A Phase I and pharmacokinetic study of the mitochondrial-specific rhodacyanine dye analog MKT 077. Clin. Cancer Res., 6: 42-49), or solid tumors of various lineages (Wadhwa R. et al., 2002. Cancer Res. 62:4434-8). This approach however, was found to be non-practicable due to MKT-077 causing irreversible kidney damage in human patients (Propper D. J. et al., 1999. Ann. Oncol., 10: 923-927), and was ineffective or suboptimally effective when used to treat cancer patients.

Another approach involves expression of mortalin antisense RNA in cancer cells for treatment of cancers characterized by compromised p53 and pRB functions and telomerase activity (Wadhwa R. et al., 2004. Reduction in mortalin level by its antisense expression causes senescence-like growth arrest in human immortalized cells. J Gene Med. 6:439-44).

This approach however, has the significant disadvantages of being only potentially relevant to cancers characterized by compromised p53 and pRB functions and telomerase activity; and of having been investigated in synthetically immortalized cells; of not having been investigated in-vivo.

A further approach involves expression of conventional or RNA-helicase-coupled hammerhead ribozymes for treatment of cancers (Wadhwa R. et al., 2003. Targeting mortalin using conventional and RNA-helicase-coupled hammerhead ribozymes. EMBO Rep. 4:595-601). This approach however, has the significant disadvantages of being only potentially relevant to synthetically immortalized cells; and of not having been investigated in-vivo.

An additional approach suggests using mortalin as molecular target for treatment of hepatitis C virus-related hepatocellular carcinoma (Takashima M. et al., 2003. Proteomics. 3:2487-93). This approach, however, has the significant disadvantages of not having been experimentally attempted, and of being limited to potential treatment of hepatitis C virus-related hepatocellular carcinoma.

Yet a further approach suggests employing inhibition of HSC70 with deoxyspergualin to increase the sensitivity of K562 human erythroleukemia cells to complement-mediated lysis (Fishelson Z. et al., 2001. Contribution of heat shock proteins to cell protection from complement-mediated lysis. Int Immunol. 13:983-991). This approach, however, has the significant disadvantages of not having been experimentally attempted in-vivo nor against primary tumor cells.

Various prior art approaches have been proposed involving increasing levels/activity of HSP70 family proteins for treating diseases associated with pathological complement-mediated cytotoxicity.

One approach involves upregulating HSP70 synthesis using the amino acid analogue L-azetidine-2-carboxylic acid for defending cells against complement-mediated lysis (Fishelson Z. et al., 2001. Contribution of heat shock proteins to cell protection from complement-mediated lysis. Int Immunol. 13:983-91). This approach, however, has the significant disadvantages of not having been experimentally attempted in-vivo, nor against affected cells of a disease associated with pathological complement-mediated cytotoxicity.

A further approach suggests upregulating HSC70 synthesis, via treatment with ethanol, butanol or hemin, to protect cells from complement-mediated cytolysis (Fishelson Z. et al., 2001. Contribution of heat shock proteins to cell protection from complement-mediated lysis. Int Immunol. 13:983-991). This approach, however, also has the significant disadvantages of not having been experimentally attempted in-vivo nor against affected cells of a disease associated with pathological complement-mediated cytotoxicity.

Another approach involves using HSP70 to inhibit complement activation for treating xenograft rejection (Gralinski M R. et al., 1996. Am J Physiol. 271:H571-8). This approach, however, has the significant disadvantage of not having been attempted experimentally.

Critically, no prior art approach involving modulation of HSP70 family member proteins for disease treatment has demonstrated satisfactory/optimal therapeutic effectiveness.

Thus, all prior art approaches have failed to provide an adequate solution for using modulation of levels/activity of HSP70 family member proteins, such as mortalin, for treatment of diseases associated with pathological complement-mediated cytotoxicity, and/or associated with pathological cells and treatable via complement-mediated cytotoxicity of such cells.

There is thus a widely recognized need for, and it would be highly advantageous to have novel, maximally effective methods of treating diseases via modulation of levels/activity of HSP70 family proteins, such as mortalin, devoid of the above limitation.

SUMMARY OF THE INVENTION

The present invention discloses a method of modulating levels/activity polypeptides at least 70 percent similar to SEQ ID NO: 1, for regulating vesicular shedding of complement, for regulating complement-mediated cytotoxicity, and for treating diseases associated with pathological cells which are treatable via such cytotoxicity directed against such cells, and/or which are associated with pathological complement-mediated cytolysis. The present invention further discloses articles of manufacture which comprise compounds for practicing such methods. These methods can be effected in a variety of ways, and these articles of manufacture may be configured in a variety of ways, as further described and exemplified hereinbelow.

According to yet another aspect of the present invention there is provided a method of treating a disease associated with a pathological cell population, the method comprising: (a) increasing an association of complement with the pathological cell population in a subject in need of treatment; and (b) decreasing a level and/or activity of a polypeptide in the pathological cell population, the polypeptide being at least 70 percent similar to SEQ ID NO: 1, thereby treating the disease.

According to further features in preferred embodiments of the invention described below, step (a) is effected by increasing an association of an antibody constant region with the pathological cell population.

According to still further features in the described preferred embodiments, step (b) is effected by administering to the subject at least one compound selected from the group consisting of: a molecule capable of binding the polypeptide; an enzyme capable of cleaving and/or modifying the polypeptide; an siRNA molecule capable of inducing degradation of an mRNA encoding the polypeptide; a DNAzyme capable of cleaving an mRNA or DNA encoding the polypeptide; an antisense polynucleotide capable of hybridizing with an mRNA encoding the polypeptide; a ribozyme capable of cleaving an mRNA encoding the polypeptide; and a non-functional analogue of at least a functional portion of the polypeptide;

According to still another aspect of the present invention there is provided an article of manufacture comprising packaging material and a pharmaceutical composition being identified in print in or on the packaging material for treatment of a disease associated with a pathological cell population, wherein the pharmaceutical composition comprises a pharmaceutically acceptable carrier, and, as active ingredients: (i) a compound for decreasing a level and/or activity of a polypeptide in the pathological cell population in a subject in need of treatment, the polypeptide being at least 70 percent similar to SEQ ID NO: 1; and (ii) a compound for increasing an association of complement with the pathological cell population.

According to further features in preferred embodiments of the invention described below, the compound for decreasing the level and/or activity of the polypeptide in the pathological cell population is a substantially cell membrane-impermeable compound.

According to a further aspect of the present invention there is provided a method of treating a disease associated with a pathological cell population, the method comprising: (a) administering to a subject in need of treatment a substantially cell membrane-impermeable compound for decreasing a level and/or activity of a polypeptide in the pathological cell population, the polypeptide being at least 70 percent similar to SEQ ID NO: 1; and (b) optionally, increasing an association of complement with the pathological cell population, thereby treating the disease.

According to further features in preferred embodiments of the invention described below, increasing the association of complement with the pathological cell population is effected by increasing an association of an antibody constant region with the pathological cell population.

According to still further features in the described preferred embodiments, increasing the association of the antibody constant region with the pathological cell population is effected by administering to the subject a compound which comprises the antibody constant region and is capable of specifically binding the pathological cell population.

According to yet a further aspect of the present invention there is provided an article of manufacture comprising packaging material and a pharmaceutical composition being identified in print in or on the packaging material for treatment of a disease associated with a pathological cell population, wherein the pharmaceutical composition comprises a pharmaceutically acceptable carrier and, as one or more active ingredients: (i) a substantially cell membrane-impermeable compound for decreasing a level and/or activity of a polypeptide in the pathological cell population, the polypeptide being at least 70 percent similar to SEQ ID NO: 1; and (ii) optionally, a compound for increasing an association of complement with the pathological cell population.

According to still further features in the described preferred embodiments, the substantially cell membrane-impermeable compound comprises an antibody or antibody fragment capable of specifically binding the polypeptide.

According to still further features in the described preferred embodiments, the compound for increasing the association of complement with the pathological cell population is a compound which comprises an antibody constant region and is capable of specifically binding the pathological cell population.

According to still further features in the described preferred embodiments, the compound which comprises the antibody constant region and is capable of specifically binding the pathological cell population is an antibody.

According to still further features in the described preferred embodiments, the compound for decreasing the level and/or activity of the polypeptide in the pathological cell population is a compound selected from the group consisting of: a molecule capable of binding the polypeptide; an enzyme capable of cleaving and/or modifying the polypeptide; an siRNA molecule capable of inducing degradation of an mRNA encoding the polypeptide; a DNAzyme capable of cleaving an MRNA or DNA encoding the polypeptide; an antisense polynucleotide capable of hybridizing with an mRNA encoding the polypeptide; a ribozyme capable of cleaving an mRNA encoding the polypeptide; and a non-functional analogue of at least a functional portion of the polypeptide.

According to still further features in the described preferred embodiments, the molecule capable of binding the polypeptide is an antibody or antibody fragment.

According to still further features in the described preferred embodiments, the antibody fragment is selected from the group consisting of a single-chain Fv, an Fab, an Fab', and an F(ab')2.

According to still further features in the described preferred embodiments, the disease associated with the pathological cell population is selected from the group consisting of a tumor, an infectious disease, an autoimmune disease and a transplantation-related disease According to one aspect of the present invention there is provided a method of treating a disease associated with pathological complement-mediated cytotoxicity, the method comprising increasing in a cell population of a subject in need of treatment a level and/or activity of a polypeptide at least 70 percent similar to SEQ ID NO: 1, thereby treating the disease.

According to further features in preferred embodiments of the invention described below, increasing in the cell population the level and/or activity of the polypeptide is effected by administering to the subject at least one compound selected from the group consisting of a polynucleotide designed and constructed to express in the cell population at least a functional portion of the polypeptide, a compound capable of increasing an expression of an endogenous DNA or mRNA encoding the polypeptide, and a molecule capable of activating the polypeptide.

According to another aspect of the present invention there is provided an article of manufacture comprising packaging material and a pharmaceutical composition being identified in print in or on the packaging material for treatment of a disease associated with pathological complement-mediated cytotoxicity, wherein the pharmaceutical composition comprises a pharmaceutically acceptable carrier and, as an active ingredient, a compound for increasing in a cell population of a subject in need of treatment a level and/or activity of a polypeptide at least 70 percent similar to SEQ ID NO: 1.

According to further features in preferred embodiments of the invention described below, the compound is selected from the group consisting of a polynucleotide capable of expressing in the cell population at least a functional portion of the polypeptide, a compound capable of increasing an expression of an endogenous DNA or mRNA encoding the polypeptide, and a compound capable of activating the polypeptide.

According to still further features in the described preferred embodiments, the disease associated with pathological complement-mediated cytotoxicity is selected from the group consisting of an autoimmune disease, an immune complex disease and a transplantation-related disease.

According to further features in preferred embodiments of the invention described below, the polypeptide is a mortalin.

According to still further features in the described preferred embodiments, the activity of the polypeptide is mediation of vesicular shedding of complement.

The present invention successfully addresses the shortcomings of the presently known configurations by providing a novel and optimally effective method of modulating levels/activity polypeptides at least 70 percent similar to SEQ ID NO: 1, for regulating vesicular shedding of complement, for regulating complement-mediated cytotoxicity, and for treating diseases associated with pathological cells which are treatable via such cytolysis of such cells, and/or which are associated with pathological complement-mediated cytolysis. The present invention further successfully addresses the shortcomings of the presently known configurations by providing novel articles of manufacture which comprise compounds for practicing this method.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2c-d are densitometric analyses of the bands shown in FIGS. 2a-b, respectively. Results are representative of 3 independent experiments. FIG. 2e demonstrates that mortalin is released by viable cells. Cells were subjected to different doses of anti-K562 antibody (dilutions: 1/3, 1/6, 1/9, 1/12, 1/15, 1/18 and 1/21) and NHS or HI-NHS. After 10 minutes at 37 degrees centigrade, supernatants released from the cells were analyzed as described above for FIG. 2a. Cells were also kept for 60 minutes at 37 degrees centigrade and their percent lysis was determined. Results show the amount of extracellular mortalin (as determined by Western blotting and densitometry) versus the level of cell death. Results are representative of 3 independent experiments. *, $p<0.005$, between 0 and 14 percent lysis.

In FIG. 3b, proteins released after 20 minutes incubation (as above) were treated with Triton-X100 (0.1 percent) and then sedimented at 100,000×g. The resultant supernatants and pellets were analyzed by SDS-PAGE and Western blotting with anti-mortalin (FIG. 3c) or anti-C9 (FIG. 3d) antibodies. Results in FIGS. 3a-b are each representative of 3 independent experiments.

FIGS. 4a-b depict assays in which K562 cells were treated with anti-K562 antibody followed by NHS, HI-NHS, C8-depleted serum (C8D) or C8D mixed with 20 micrograms per milliliter C8 (C8D+C8). After 10 minutes at 37 degrees centigrade, the cells were washed and incubated for 10 minutes at 37 degrees centigrade. Supernatants were collected and analyzed by SDS-PAGE and Western blotting with anti-mortalin antibodies. Densitometric analysis of 3 independent experiments is shown in FIG. 4b. FIG. 4c depicts an assay in which K562 cells were treated with a sublytic dose mellitin (70 micromolar) or with PBS as control. After 10 minutes at 37 degrees centigrade, the cells were washed and incubated for different times at 37 degrees centigrade. Supernatants were collected and analyzed by SDS-PAGE and Western blotting with anti-mortalin antibodies. Densitometric analysis of 3 independent experiments is shown. FIG. 4d depicts an assay in which cells were treated with a sublytic dose of streptolysin O (SLO, 900 units per milliliter) or with DTT as control. After 10 minutes at 37 degrees centigrade, the cells were washed and incubated for different times at 37 degrees centigrade. Supernatants were collected and analyzed by SDS-PAGE and Western blotting with anti-mortalin antibodies. Densitometric analysis of 3 independent experiments is shown. Cells treated with NHS or HI-NHS were also included in FIGS. 4c-d, as described for FIG. 4a. Statistical analyses indicated a significant ($p<0.01$) difference between the NHS and C8D+C8 groups and all other groups.

FIG. 5a depicts an assay in which K562 cells were treated with anti-mortalin antibodies or a prebleed serum (diluted 1:500) mixed with anti-K562 antibodies (diluted 1:30 or 1:40) and then with NHS or HI-NHS. After 60 minutes at 37 degrees centigrade, cell lysis was determined via Trypan blue staining. Results are representative of 3 independent experiments. FIG. 5b depicts an assay in which K562 cells were treated with anti-mortalin antibodies (diluted 1:30 or 1:40) and C8D (or HI-NHS as negative control). After 15 minutes at 37 degrees centigrade, the cells were washed and mixed with C7-deficient human serum (C7D) containing 20 millimolar EDTA (or HI-NHS and EDTA). The C7D was pre-mixed with anti-mortalin antibodies (1:500) or prebleed serum (or buffer control). Cell lysis was determined as described above. *, $p<0.01$ between groups with anti-mortalin antibodies and prebleed serum.

FIG. 6e depicts an assay in which metabolically-labeled K562 cells were pre-treated for 30 minutes at 37 degrees centigrade with PBS, 100 micrograms per milliliter PMB, 0.1 percent DMSO or 10 micromolar PD. The cells were then treated with anti-K562 antibody and NHS or HI-NHS for 30 minutes at 37 degrees centigrade. Radioactivity in cell supernatants was determined. Results are representative of 3 independent experiments. FIGS. 6f-g depict results from assays in which cells pretreated with PMB (FIG. 6f) or PD98059 (FIG. 6g), as for FIGS. 6a-d, were subjected to a complement-induced protection assay, performed as described in the Materials and Methods section, above. Percent cell lysis following a 1 hour incubation with NHS or HI-NHS diluted 1:4 or 1:6 is shown. *, p<0.05.

FIG. 7 is a pair of protein-protein binding assay photographs depicting that mortalin binds to complement C9. Complement C9 and BSA (5 micrograms each) were subjected to SDS-PAGE and transferred to a nitrocellulose membrane. The membrane was then incubated with K562 cell lysate pre-mixed with PBS (Cell lysate) or with 5 micrograms per milliliter C9 (Cell lysate+C9). A protease inhibitor cocktail was included to block proteases in the cell lysates. Membranes were then washed and analyzed by Western blotting with anti-mortalin antibodies. Results are representative of 3 independent experiments.

FIGS. 8a-b are Western immunoblotting and cytotoxicity assay data depicting that elevation of mortalin level by treatment with cathepsin L inhibitor protects cells from complement-mediated lysis. FIG. 8a depicts results of an assay in which K562 cells (40 million cells per milliliter) were treated with 5, 10, 20 or 40 micromolar of cathepsin L inhibitor (Z-Phe-Phe-CH2F) or with 0.2 percent DMSO as control for 30 minutes at 37 degrees centigrade. Cells which were not treated (NT) were also used as control. Following incubation, the cells were lysed in lysis buffer, protein concentration was measured and equal amounts of protein were analyzed by SDS-PAGE and Western Blotting using anti-mortalin antibody. Results are representative of 3 independent experiments. FIG. 8b depicts results of an assay in which K562 cells (40 million cells per milliliter) were pretreated with 10 micromolar cathepsin L inhibitor or with 0.05 percent DMSO as control for 30 minutes at 37 degrees centigrade. Next, the cells were treated with anti-K562 antibodies diluted 1:40 or 1:50 and with HI-NHS or NHS. Lysis was measured following 60 minutes incubation at 37 degrees centigrade. Results are representative of 3 independent experiments. Statistical analysis indicated a significant (*, p<0.05) difference between the group treated with DMSO and the group treated with cathepsin L inhibitor.

FIG. 9 is a histogram of cell lysis assay results depicting that overexpression of mortalin protects cells from complement-mediated lysis. K562 cells were stably transfected with pGFPC1-mortalin plasmid or with pGFPC1 empty vector as control. Cells were grown in RPMI medium containing G418 selection reagent. Cells (40 million cells per milliliter) were treated with anti-K562 antibodies diluted 1:40, 1:50 or 1:60 and with HI-NHS or NHS. Lysis was measured following 60 minutes incubation at 37 degrees centigrade. Results are representative of 3 independent experiments. Statistical analysis indicated a significant (*, p<0.01) difference between the cells transfected with the empty vector and the cells transfected with the mortalin-containing vector.

DESCRIPTION OF THE PREFERRED EMBODIMENTS

Figures 1A, 1B:
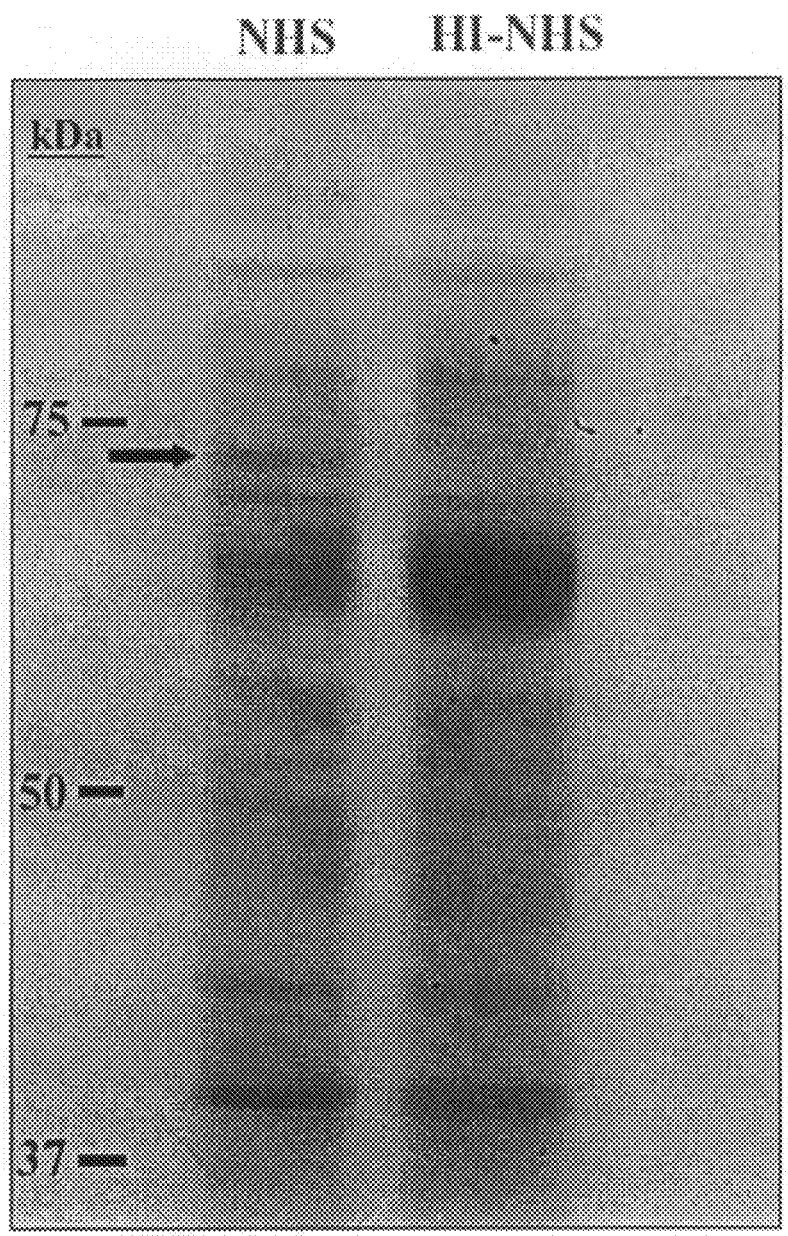
FIG. 1a is a photograph of an SDS-PAGE assay depicting specifically release of a 75 kDa protein by K562 cells attacked by sublytic complement. K562 cells were treated with a sublytic dose of anti-K562 antibody and NHS or HI-NHS. After 60 minutes at 37 degrees centigrade the cells were sedimented and the supernatants were subjected to SDS-PAGE (5.5 micrograms/lane) and the gel was silver-stained. The arrow points at a protein that appears stronger in NHS-treated cells than in HI-NHS-treated cells.
FIG. 1b is a set of amino acid sequences of fragments of the 75 kDa protein specifically released by K562 cells attacked by sublytic complement, identifying the released protein as mortalin. The 75 kDa protein was excised from a Coomassie Blue-stained gel following SDS-PAGE of released proteins, and was analyzed by MALDI-MS. Seven peptides were identified; all of them corresponded to mortalin.

The present invention is of a method of treating a disease associated with a pathological cell population, which is effected by increasing an association of complement with the pathological cell population in a subject in need of treatment, and by decreasing a level and/or activity of a polypeptide in the pathological cell population, where the polypeptide is at least 70 percent similar to SEQ ID NO: 1; and is further of an article of manufacture which comprises packaging material and a pharmaceutical composition and which is identified in print in or on the packaging material for treatment of a disease associated with a pathological cell population, where the pharmaceutical composition comprises a pharmaceutically acceptable carrier, and, as active ingredients, a compound for decreasing a level and/or activity of the polypeptide, and a compound for increasing the association.

The present invention is further of a method of treating a disease associated with a pathological cell population, which is effected by: administering to a subject in need of treatment a substantially cell membrane-impermeable compound for decreasing a level and/or activity of the polypeptide in the pathological cell population; and, optionally, increasing an association of complement with the pathological cell population; and is further of an article of manufacture which comprises packaging material and a pharmaceutical composition, and which is identified in print in or on the packaging material for treatment of a disease associated with a pathological cell population, where the pharmaceutical composition comprises a pharmaceutically acceptable carrier and, as one or more active ingredients: a substantially cell membrane-impermeable compound for decreasing a level and/or activity of the polypeptide in the pathological cell population; and, optionally, a compound for increasing the association of complement with the pathological cell population.

The present invention is yet further of a method of treating a disease associated with pathological complement-mediated cytotoxicity, which is effected by increasing in a cell population of a subject in need of treatment a level and/or activity of the polypeptide; and is further of an article of manufacture which comprises packaging material and a pharmaceutical composition, and which is identified in print in or on the packaging material for treatment of a disease associated with pathological MAC-mediated cytotoxicity, where the pharmaceutical composition comprises a pharmaceutically acceptable carrier and, as an active ingredient, a compound for increasing in a cell population of a subject in need of treatment a level and/or activity of the polypeptide.

Specifically, the present invention can be used for effectively regulating vesicular shedding of complement and for regulating complement-mediated cytotoxicity. As such, the present invention can be used for optimally treating diseases, such as such as tumoral, infectious, autoimmune and transplantation-related diseases, which are associated with pathological cells and are treatable via complement-mediated cytolysis of such cells, and/or diseases, such as autoimmune, immune-complex and transplantation-related diseases, which are associated with pathological complement-mediated cytolysis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases such as tumoral, infectious, autoimmune and transplantation-related diseases, which are associated with pathological cells and are treatable via complement-mediated cytolysis of such cells represent numerous highly debilitating and/or lethal diseases for which no optimal therapy exists. Similarly, diseases associated with pathological complement-mediated cytotoxicity, such as autoimmune, immune-complex and transplantation-related diseases, also represent numerous highly debilitating and/or lethal diseases for which no optimal therapy exists. In view of the possible role of HSP70 family proteins in mediating downregulation of complement-mediated cytotoxicity, and in view of the overexpression of such proteins in pathological cells susceptible to elimination via such cytotoxicity, suitable modulation of levels/activity of such proteins may represent a potentially optimal strategy for treating such diseases.

Various approaches involving decreasing levels/activity of HSP70 family proteins, such as mortalin, for treating diseases associated with pathological cells and treatable via complement-mediated cytolysis of such cells have been described in the prior art. Such approaches involve administration of the mortalin inhibitor MKT-077 (formerly FJ-776) for treatment of cancers characterized by wild-type p53 (Wadhwa R. et al., 2000. Cancer Research 60, 6818-6821), chemo-resistant solid tumors (Propper D. J. et al., 1999. Phase I trial of the selective mitochondrial toxin MKTO77 in chemo-resistant solid tumours. Ann. Oncol., 10: 923-927), untreatable/treatment-refractory solid tumors (Britten C. D. et al., 2000. A Phase I and pharmacokinetic study of the mitochondrial-specific rhodacyanine dye analog MKT 077. Clin. Cancer Res., 6: 42-49), or solid tumors of various lineages (Wadhwa R. et al., 2002. Cancer Res. 62:4434-8). This approach however, was found to be non-practicable due to MKT-077 causing irreversible kidney damage in human patients (Propper D. J. et al., 1999. Ann. Oncol., 10: 923-927), and was ineffective or suboptimally effective when used to treat cancer patients. Such approaches further involve expression of mortalin antisense RNA in cancer cells for treatment of cancers characterized by compromised p53 and pRB functions and telomerase activity (Wadhwa R. et al., 2004. Reduction in mortalin level by its antisense expression causes senescence-like growth arrest in human immortalized cells. J Gene Med. 6:439-44). This approach however, has the significant disadvantages of being only potentially relevant to cancers characterized by compromised p53 and pRB functions and telomerase activity; and of having been investigated in synthetically immortalized cells; of not having been investigated in-vivo. Such approaches yet further involve expression of conventional or RNA-helicase-coupled hammerhead ribozymes for treatment of cancers (Wadhwa R. et al., 2003. Targeting mortalin using conventional and RNA-helicase-coupled hammerhead ribozymes. EMBO Rep. 2003 June;4(6):595-601). This approach however, has the significant disadvantages of being only potentially relevant to synthetically immortalized cells; and of not having been investigated in-vivo. Such approaches still further involve using mortalin as molecular target for treatment of hepatitis C virus-related hepatocellular carcinoma (Takashima M. et al., 2003. Proteomics. 3:2487-93). This approach, however, has the significant disadvantages of not having been experimentally attempted, and of being limited to potential treatment of hepatitis C virus-related hepatocellular carcinoma. Such approaches additionally involve employing inhibition of HSC70 with deoxyspergualin to increase the sensitivity of K562 human erythroleukemia cells to complement-mediated lysis (Fishelson Z. et al., 2001. Contribution of heat shock proteins to cell protection from complement-mediated lysis. Int Immunol. 13:983-991). This approach, however, has the significant disadvantages of not having been experimentally attempted in-vivo nor against primary tumor cells.

Various approaches involving increasing levels/activity of HSP70 family proteins for treating diseases associated with pathological complement-mediated cytotoxicity have been described in the prior art. Such approaches involve upregulating HSP70 synthesis using the amino acid analogue L-azetidine-2-carboxylic acid for defending cells against complement-mediated lysis (Fishelson Z. et al., 2001. Contribution of heat shock proteins to cell protection from complement-mediated lysis. Int Immunol. 13:983-91). This approach, however, has the significant disadvantages of not having been experimentally attempted in-vivo, nor against affected cells of a disease associated with pathological complement-mediated cytotoxicity. Such approaches further involve upregulating HSC70 synthesis, via treatment with ethanol, butanol or hemin, to protect cells from complement-mediated cytolysis (Fishelson Z. et al., 2001. Contribution of heat shock proteins to cell protection from complement-mediated lysis. Int Immunol. 13:983-991). This approach, however, also has the significant disadvantages of not having been investigated in-vivo nor against affected cells of a disease associated with pathological complement-mediated cytotoxicity. Such approaches yet further involve using HSP70 to inhibit complement activation for treating xenograft rejection (Gralinski M R. et al., 1996. Am J Physiol. 271:H571-8). This approach, however, has the significant disadvantage of not having been attempted experimentally.

Thus, the prior art fails to provide satisfactory/optimal means of harnessing modulation of levels/activity of HSP70 family proteins for treating diseases by regulation of complement-mediated cytotoxicity.

Figure 5A:
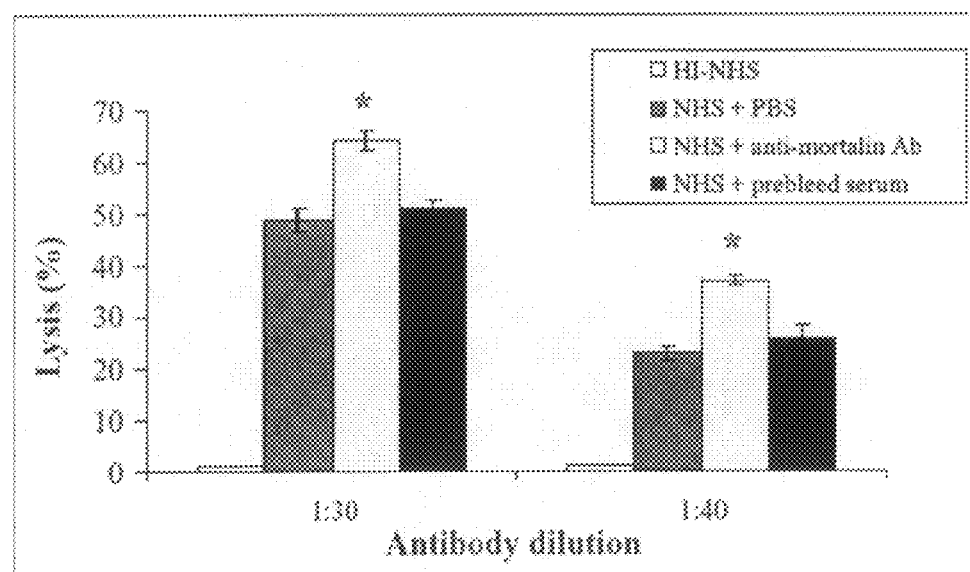
FIGS. 5a-b are histograms depicting that anti-mortalin antibodies promote cell death by complement complex C5b-9.
Figure 5B:
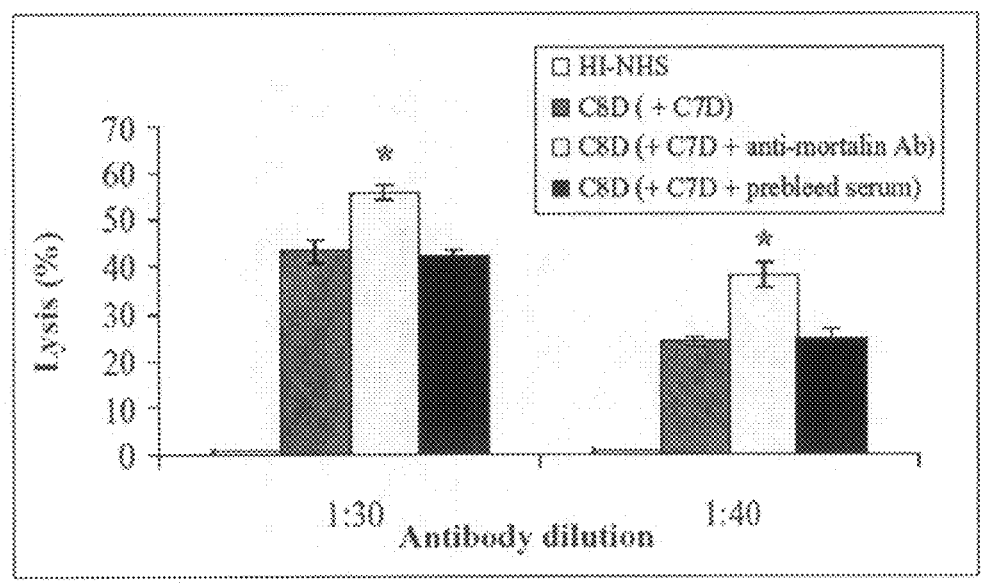

While reducing the present invention to practice it was uncovered that decreasing levels/activity of an HSP70 family protein such as mortalin in pathological cells such as tumor cells using a cell membrane-impermeable compound, such as an antibody specific for the protein, while concomitantly increasing association of complement with the pathological cells, could be used to effectively decrease vesicular shedding of complement from the tumor cells, and to effectively increase complement-mediated cytolysis of the tumor cells (refer, for example, to FIGS. 5a-b of the Examples section below).

Conversely, it was further uncovered while reducing the present invention to practice that increasing levels/activity of mortalin in cells subjected to complement-mediated cytotoxicity could be used to effectively decrease such cytotoxicity in such cells (refer, for example, to FIGS. 8a-b, and 9 of the Examples section which follows).

As such, it is presently taught for the first time that decreasing levels/activity of an HSP70 family protein, such as mortalin, in pathological cells, such as tumor cells, in a subject having a disease associated with such cells, such as a tumor, while concomitantly increasing an association of complement with the cells, can be used to effectively decrease vesicular shedding of complement from such cells, to effectively increase complement-mediated cytolysis of such cells, and to effectively treat such a disease in such a subject. It will be appreciated that this presently taught disease treatment method is clearly novel and non-obvious over the prior art, since although decreasing in pathological cells, such as tumor cells, levels/activity of an HSP70 family protein, such as mortalin, and antibody/complement-mediated cytolysis of such cells have separately been attempted in the prior art for tumor treatment, decreasing such activity/levels was not found to be therapeutically suitable in the prior art, and the prior art provides no motivation for treating such a disease by combining decreasing of such activity/levels in such cells with increasing association of complement with such cells. In very sharp contrast to prior art teachings, however, the non-obvious teaching is provided for the first time whereby decreasing such activity/levels in pathological cells can be used to significantly enhance complement-mediated cytolysis of the cells. Hence, the non-obvious teaching is presently provided for the first time whereby decreasing activity/levels of an HSP70 family protein such as mortalin in pathological cells in a subject having a disease associated with such cells, while concomitantly increasing an association of complement with the cells, can be used to achieve optimal complement-mediated cytolysis of such cells and effective treatment of such a disease.

Further as such, it is further presently taught for the first time that administration of a substantially cell membrane-impermeable compound, such as an antibody, for decreasing activity/levels of an HSP70 family protein, such mortalin, to a subject having a disease, such as a tumor, which is associated with pathological cells, such as tumor cells, can be used to effectively decrease vesicular shedding of complement from such cells, to effectively increase complement-mediated cytolysis of such cells, and to effectively treat the disease in the subject. It will be appreciated that this presently taught disease treatment method is also clearly novel and non-obvious over the prior art, since although decreasing levels/activity of an HSP70 family protein, such as mortalin, in pathological cells, such as tumor cells, has been attempted in the prior art for tumor treatment, the prior art teaches that the relevant activity of an HSP70 family protein such as mortalin is intracellular, and concomitantly that such activity must be decreased by administration of membrane-permeable compounds capable of inhibiting the activity intracellularly, as exemplified by the aforementioned prior art approach involving administration of the cell membrane-permeable mortalin inhibitor MKT-077 for tumor treatment. In very sharp contrast to prior art teachings, however, the non-obvious teaching is presently provided for the first time whereby administration to a subject having a disease associated with pathological cells of a substantially cell membrane-impermeable compound, such as an antibody, for decreasing levels/activity in such cells of an HSP70 family protein such as mortalin can be used to achieve optimal complement-mediated cytolysis of such cells and effective treatment of such a disease in such a subject.

Yet further as such, it is presently taught for the first time that increasing levels/activity of an HSP70 family protein, such as mortalin, in cells subjected to pathological complement-mediated cytotoxicity, in a subject having a disease associated with such cytotoxicity can be used to effectively increase vesicular shedding of complement from such cells, to effectively decrease such complement-mediated cytotoxicity, and to effectively treat such a disease in such a subject. It will be appreciated that this presently taught disease treatment method is clearly novel and non-obvious over the prior art, since the prior art fails to teach any method of decreasing pathological complement-mediated cytolysis of cells by increasing such activity/levels.

Thus, the present invention can be used to effectively treat a disease which is associated with pathological cells and/or which is associated with pathological complement-mediated cytotoxicity.

Thus, according to one aspect of the present invention there is provided a method of treating a disease associated with a pathological cell population. The method is effected by decreasing a level and/or activity of a polypeptide in a pathological cell population of a subject in need of treatment, where the polypeptide is at least 70 percent similar to SEQ ID NO: 1.

According to one embodiment, the method of treating the disease associated with the pathological cell population further comprises increasing an association of complement with the pathological cell population.

According to an alternate embodiment, the method of treating the disease associated with the pathological cell population is effected by administering to the subject a substantially cell membrane-impermeable compound for decreasing the level and/or activity of the polypeptide in the pathological cell population, and preferably by further increasing an association of complement with the pathological cell population.

As used herein, the term "treating" when relating to a disease of the present invention refers to preventing onset of the disease, alleviating, attenuating, palliating or eliminating the symptoms of a disease, slowing, reversing or arresting the progression of the disease, or curing the disease.

As used herein, the term "pathological" when relating to a pathological cell population of the present invention refers to a cell population whose elimination in a subject of the present invention having a disease associated with such a cell population can be used to treat the disease in the subject. The pathological cell population may be any nucleated cell population derived from an organism which expresses a mortalin.

As used herein, the term "decreasing" when relating to the level/activity of the polypeptide refers to preventing, reducing, inhibiting, downregulating and/or eliminating the level/activity.

As used herein, the activity/level of the polypeptide "in" the pathological cell population refers to an intracellular, cell membranal, cell surface and/or cell-proximal level/activity of the polypeptide.

As used herein, the phrase "subject in need of treatment" refers to a subject which has the disease, or which is susceptible to having the disease. The subject may be any organism having an immune system capable of complement-mediated cytolysis. Preferably, the subject is a homeotherm, more preferably a mammal, more preferably a primate and most preferably a human.

As used herein, the term "increasing" when relating to an association of complement with a pathological cell population of the present invention refers to inducing, stimulating, promoting, increasing and/or upregulating the association.

As used herein, the term "complement" when relating to an association of complement with a pathological cell population of the present invention, refers to any complement protein, or any complex of complement proteins, including activated complement C1, C3 and C4 which are capable of attaching (bridging) between leukocytes and lymphocytes and nucleated cells and complement membrane attack complex (MAC)/C5b-9, which is capable of facilitating cytolysis of a nucleated cell.

The method according to this aspect of the present invention, by virtue of enabling decreasing of vesicular shedding of complement by a pathological cell population, and enabling increasing of complement-mediated cytolysis of a pathological cell population, can be used to treat any of various diseases associated with a pathological cell population, including tumoral, infectious, autoimmune and transplantation-related diseases. It will be appreciated that a tumoral disease is associated with pathological tumor cells; that an infectious disease such as an intracellular pathogen infection, is associated with pathological pathogen-infected cells; that an autoimmune disease, such as one associated with immune cells such as T-lymphocytes or B-lymphocytes/antibodies specific for an autoantigen, or NK cells, is associated with such pathological immune cells; and that a transplantation-related disease such as graft rejection or graft-versus-host disease (GVHD), is associated with pathological recipient lymphocytes targeting graft antigens or pathological graft lymphocytes targeting autoantigens, respectively. As such, it will be appreciated that the method according to this aspect of the present invention can be used to treat such diseases by inducing cytolysis of such respective pathological cells associated therewith, in accordance with the teachings of the present invention, as described further hereinbelow.

Preferably, the polypeptide has a percent similarity to SEQ ID NO: 1 of at least 75 percent, more preferably of at least 80 percent, more preferably of at least 85 percent, more preferably of at least 90 percent, more preferably of at least 91 percent, more preferably of at least 92 percent, more preferably of at least 93 percent, more preferably of at least 94 percent, more preferably of at least 95 percent, more preferably of at least 96 percent, more preferably of at least 97 percent, more preferably of at least 98 percent, more preferably of at least 99 percent, and more preferably of 100 percent. More preferably, the polypeptide of the present invention comprises the amino acid sequence set forth in SEQ ID NO: 1, and most preferably has the amino acid sequence set forth in SEQ ID NO: 1. The amino acid sequence set forth in SEQ ID NO: 1 corresponds to human mortalin (GenBank Identifier gi:24234688).

Alternately, the polypeptide may comprise the amino acid sequence corresponding to human mortalin identified by GenBank Accession NP_004125.3 (SEQ ID NO: 2), which is 92 percent similar to SEQ ID NO: 1, or more preferably the amino acid sequence of human mortalin corresponding to GenBank Accession AAH30634.1 (SEQ ID NO: 3), which is 94 percent similar to SEQ ID NO: 1.

As used herein, the "percent similarity" of a test amino acid sequence (that of the polypeptide of the present invention) relative to a reference amino acid sequence (SEQ ID NO: 1) corresponds to the percent amino acid homology obtained ("Positives" output) when comparing the reference sequence against the test sequence using the PROTEIN-PROTEIN BASIC LOCAL ALIGNMENT SEARCH TOOL (BLAST) [blastp] software of the National Center for Biotechnology Information (NCBI; ncbidotnlmdotnihdotgov/BLAST/).

Decreasing the level/activity of the polypeptide in the pathological cell population can be achieved in any of various ways.

Decreasing the level/activity of the polypeptide in the pathological cell population is preferably effected so as to maximally decrease, and more preferably so as to essentially completely eliminate, the activity of the polypeptide in the pathological cell population, so as to achieve optimal complement-mediated cytolysis of the pathological cell population, and hence optimal disease treatment.

Preferably, the level/activity of the polypeptide is vesicular shedding of complement from the pathological cell population, and more preferably is inhibition of complement-mediated cytolysis of the pathological cell population.

Decreasing the level/activity of the polypeptide in the pathological cell population may be effected by administering to the subject a compound such as a molecule capable of binding the polypeptide, an enzyme capable of cleaving and/or modifying the polypeptide, an siRNA molecule capable of inducing degradation of an mRNA encoding the polypeptide, a DNAzyme capable of cleaving an mRNA or DNA encoding the polypeptide, an antisense polynucleotide capable of hybridizing with an mRNA encoding the polypeptide, a ribozyme capable of cleaving an mRNA encoding the polypeptide, and/or a non-functional analogue of at least a functional portion of the polypeptide.

Preferably, the molecule capable of binding the polypeptide is an antibody fragment, more preferably an antibody, and most preferably a polyclonal antibody.

The antibody or antibody fragment may be advantageously derived from an organism, such as rabbit, which is xenogeneic with the subject.

As is described in Example 1 of the Examples section below, a rabbit-derived polyclonal antibody which is specific for the pathological cells can be used to significantly enhance vesicular shedding of mortalin from pathological cells, and to significantly enhance complement-mediated lysis of pathological cells.

Ample guidance is provided hereinbelow for suitably obtaining and using antibodies or antibody fragments for decreasing the level/activity of a polypeptide of the present invention in a pathological cell population of the present invention.

As is disclosed in the Examples section below a polypeptide of the present invention such as mortalin specifically binds complement C9 (refer, for example, to FIG. 7), or to a lesser extent complement C8. Without being bound to a paradigm, the present inventors are of the opinion such binding interactions are involved in increase of vesicular shedding of complement, and decrease of complement-mediated cytolysis mediated by a polypeptide of the present invention such as mortalin. As such, the molecule capable of binding the polypeptide so as to decrease the level/activity thereof may alternately be a minimal fragment of a polypeptide of the present invention, such as mortalin, capable of specifically binding a molecule, such as complement C8, or more preferably C9; or a minimal fragment of complement C8, or more preferably C9, capable of specifically binding a polypeptide of the present invention, such as mortalin.

As described hereinabove, according to one embodiment of the presently disclosed method of treating the disease associated with a pathological cell population, the compound for decreasing the level/activity of the polypeptide is a substantially cell membrane-impermeable compound. Preferably, the substantially membrane-impermeable compound is not capable of diffusing through the cell-membrane of cells of a pathological cell population of the present invention. Such a substantially membrane-impermeable compound is preferably a hydrophilic polypeptide, more preferably an antibody specific for the polypeptide, as described herein. It will be well within the purview of one of ordinary skill in the art to select an alternate type of suitable substantially membrane-impermeable compound for decreasing the level/activity of the polypeptide, such as one capable of specifically binding the polypeptide. An advantage of a substantially cell membrane-impermeable therapeutic agent over a cell membrane-permeable agent is minimal risk of side-effects resulting from interactions of the agent with intracellular molecules.

As described hereinabove, decreasing the level/activity of the polypeptide in the pathological cell population may be effected by administering to the subject a compound such as a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr Opin Genetics and Development 12:225-232 (2002); and Bernstein, Nature 409: 363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr Op Gen Develop. 12:225-232 (2002); Hammond et al., 2001. Nat Rev Gen. 2:110-119 (2001); and Sharp Genes Dev. 15:485-90 (2001)]. Although the mechanism of cleavage is still to be elucidated, research indicates that each RISC contains a single siRNA and an RNase [Hutvagner and Zamore, Curr Opin Gen. Develop. 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al., Nat Rev Gen. 2:110-119 (2001), Sharp Genes Dev. 15:485-90 (2001); Hutvagner and Zamore Curr Opin Gen. Develop. 12:225-232 (2002)]. Ample guidance for using RNAi to practice the present invention is provided in the literature of the art [refer, for example, to: Tuschl, ChemBiochem. 2:239-245 (2001); Cullen, Nat Immunol. 3:597-599 (2002); and Brantl, Biochem Biophys Acta 1575:15-25 (2002)].

Synthesis of RNAi molecules suitable for use with the present invention can be effected as follows. First, the mRNA sequence encoding the polypeptide of the present invention is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs), being enriched in regulatory protein binding sites. UTR-binding proteins and/or translation initiation complexes may interfere with binding of the siRNA endonuclease complex [Tuschl, Chem Biochem. 2:239-245]. It will be appreciated though, that siRNAs directed at untranslated regions may also be effective, as demonstrated for GAPDH wherein siRNA directed at the 5' UTR mediated approximately 90% decrease in cellular GAPDH mRNA and completely abolished protein level (ambiondotcom/techlib/tn/91/912dothtml).

Second, potential target sites are compared to an appropriate genomic database (e.g., human, mouse, rat etc.) using any sequence alignment software, such as the BLAST software available from the NCBI server (ncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

As is described in the Examples section which follows (refer, for example, to FIG. 10), siRNA can be used for decreasing levels/activity of a polypeptide of the present invention (human mortalin) so as to enable enhanced complement-mediated cytolysis of pathological cells.

As described hereinabove, decreasing the level/activity of the polypeptide in the pathological cell population may be effected by administering to the subject a compound such as a DNAzyme molecule capable of specifically cleaving an mRNA transcript or DNA sequence of the polypeptide. DNAzymes are single-stranded polynucleotides which are capable of cleaving both single and double stranded target sequences (Breaker, R. R. and Joyce, G. Chemistry and Biology, 1995, 2:655; Santoro, S. W. and Joyce, G. F. Proc. Natl. Acad. Sci. U. S. A., 1997, 943:4262). A general model (the "10-23" model) for the DNAzyme has been proposed. Namely, "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions [Santoro, S. W. and Joyce, G. F. Proc. Natl. Acad. Sci. U. S. A., 1997, 943:4262; for review of DNAzymes, refer, for example, to Khachigian, L M., Curr Opin Mol Ther. 4:119-21 (2002)].

Examples of construction and amplification of synthetic, engineered DNAzymes recognizing single and double-stranded target cleavage sites have been disclosed in U.S. Pat. No. 6,326,174 to Joyce et al., in which DNAzymes of similar design directed against the human urokinase receptor were recently observed to inhibit urokinase receptor expression, and successfully inhibit colon cancer cell metastasis in vivo (Itoh et al , 20002, Abstract 409, Ann Meeting Am Soc Gen Ther., asgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

As described hereinabove, decreasing the level/activity of the polypeptide in the pathological cell population may be effected by administering to the subject a compound such as an antisense polynucleotide capable of specifically hybridizing with an mRNA transcript encoding the polypeptide.

Design of antisense molecules which can be used to efficiently prevent cellular production of the polypeptide must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example: Luft, J Mol Med. 76:75-6 (1998); Kronenwett et al., Blood 91:852-62 (1998); Rajur et al., Bioconjug Chem. 8:935-40 (1997); Lavigne et al., Biochem Biophys Res Commun. 237:566-71 (1997) and Aoki et al., (1997) Biochem Biophys Res Commun. 231:540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al., Biotechnol Bioeng 65:1-9 (1999)]. Such algorithms have been successfully used to implement an antisense approach in cells. For example, the algorithm developed by Walton et al., enabled scientists to successfully design antisense oligonucleotides for rabbit beta-globin and mouse tumor necrosis factor-alpha transcripts. The same research group has also reported that the antisense activity of rationally selected oligonucleotides against three model target mRNAs in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16:1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther. 1:372-85 (1999)], while treatment of hematological malignancies via antisense oligonucleotides targeting c-myb gene, p53 and Bcl-2 had entered clinical trials and had been shown to be tolerated by patients [Gewirtz, 1999. Curr Opin Mol Ther. 1:297-306].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Decreasing levels/activity of a polypeptide of the present invention (human mortalin) in pathological cells of the present invention using antisense RNA has been described in the literature of the art (refer, for example, to Wadhwa R. et al., 2004. Reduction in mortalin level by its antisense expression causes senescence-like growth arrest in human immortalized cells. J Gene Med. 6:439-44).

As described hereinabove, decreasing the level/activity of the polypeptide in the pathological cell population may be effected by administering to the subject a compound such as a ribozyme molecule capable of specifically cleaving an MRNA transcript encoding the polypeptide.

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. The effectiveness of ribozymes has also been demonstrated in studies involving transgenic animals, gene target validation and/or pathway elucidation. Several ribozymes have been investigated in clinical trials. ANGIOZYME was the first chemically synthesized ribozyme to be studied in human clinical trials. ANGIOZYME specifically inhibits formation of vascular endothelial growth factor receptor, a key component in the angiogenesis pathway. HEPTAZYME, a ribozyme designed to selectively destroy hepatitis C virus RNA, was found effective in decreasing hepatitis C viral RNA in cell culture assays (Ribozyme Pharmaceuticals, Incorporated).

Decreasing levels/activity of a polypeptide of the present invention (human mortalin) in pathological cells of the present invention using ribozymes has been described in the literature of the art (refer, for example, to Wadhwa R. et al., 2003. Targeting mortalin using conventional and RNA-helicase-coupled hammerhead ribozymes. EMBO Rep. 4:595-601).

Decreasing the level/activity of the polypeptide in the pathological cell population may be effected by administering to the subject any of various biochemical inhibitors of an activity of the polypeptide. Such biochemical inhibitors include inhibitors of PKC, such as polymyxin B, and inhibitors of MEK, such as PD98059. As is described in the Examples section below, such inhibitors can be used to increase complement-mediated cytolysis of pathological cells (refer, for example, to FIGS. 6f and 6g).

Thus, it will be well within the purview of one of ordinary skill in the art to suitably decrease the level/activity of the polypeptide in the pathological cell population in accordance with the teachings of the present invention and/or according to any of various prior art methods.

According to the teachings of the present invention, increasing an association of complement concomitantly with decreasing the level and/or activity of the polypeptide can be advantageously used for augmenting cytolysis of the pathological cells in a pathological/therapeutic context wherein there is association of complement with the pathological cells at supra-lytic levels in the subject. Alternately, increasing the association can be used for inducing cytolysis of pathological cells in a pathological/therapeutic context wherein there is no association of complement with the pathological cells, or where the association occurs at sub-lytic levels, in the subject.

Increasing the association of complement with the pathological cell population may be effected in any one of various ways which can be used to induce complement-mediated cytolysis of the pathological cells.

In order to induce complement-mediated cytolysis of the pathological cells, increasing the association of complement with the pathological cells is optimally effected by increasing the association of complement membrane attack complex (MAC) with the pathological cells. Membrane attack complex is normally composed of complement proteins C5b, C6, C7, C8 and C9 proteins, and may be referred to as "C5b-9" herein and in the art (Muller-Eberhard, H. J. 1986. Annu Rev Immunol 4:503). It will be appreciated that increasing an association of complement membrane attack complex with the pathological cell population can be used to facilitate cytolysis of the pathological cells, thereby facilitating treatment of the disease.

In order to achieve optimally effective complement-mediated cytolysis of the pathological cell population, and/or in order to achieve complement-mediated cytolysis of the pathological cell population with minimal cytolysis of cells other than the targeted pathological cell population, as will generally be the case to avoid harmful side-effects, increasing the association of complement with the pathological cell population is optimally effected by increasing association of complement specifically with the pathological cell population.

Preferably, increasing the association of complement with the pathological cell population is effected by administering to the subject an antibody capable of binding the pathological cells. Preferably, the antibody includes a constant region which enables initiation of the classical pathway of complement activation. The antibody constant region enabling initiation of the classical pathway of complement activation is preferably the constant region of Ig(mu) or Ig(gamma), the heavy chains of antibodies having the IgM or IgG isotype, respectively. Thus, natural antibodies having a constant region capable of initiating the classical pathway of complement activation are typically of the IgM or IgG isotype. It will be appreciated that administering to the subject an antibody capable of specifically binding the pathological cells and having a constant region capable of initiating the classical pathway of complement activation will facilitate membrane attack complex assembly at the cell surface of cells of the pathological cell population and will result in concomitant complement-mediated cytolysis of the pathological cells.

Increasing the association of complement with the pathological cell population can be achieved by administering to the subject essentially any compound which comprises a moiety capable of initiating assembly of attack complex such as a suitable antibody constant region, and which further comprises a moiety capable of specifically binding the pathological cell population.

It will be appreciated that the compound may be assembled at the surface of cells of the pathological population by administering to the subject a first compound which can specifically bind the pathological cells, and a second compound which can specifically bind the first compound and which comprises a suitable antibody constant region for initiating complement mediated cytolysis. Such a scheme can be performed with enhanced safety by administering to the subject the first compound, allowing the first compound to specifically bind to the pathological cells and allowing the weakly/non-specifically bound or unbound molecules thereof to exit the circulation, and only afterwards administering to the subject the second compound. The first and second compounds may be conjugated to complementary affinity binding moieties, such as streptavidin and biotin, so as to achieve optimally rapid, specific and stable binding therebetween following administration of the second compound. Increasing the association of complement with the pathological cell population according to such a scheme will result in minimal non-specific association of the antibody constant region with, and concomitant cytolysis of, cells other than the pathological cell population.

Examples of types of suitable moieties capable of specifically binding a pathological cell population of the present invention include antibody fragments capable of specifically binding surface molecules of the pathological cells, and specific biological ligands of cell surface molecules of the pathological cells.

It will be well within the purview of one of ordinary skill in the art to obtain a compound which comprises a moiety capable of specifically binding a target antigen conjugated to an antibody constant region. For example, a fusion protein which comprises a non-immunoglobulin polypeptide moiety capable of specifically binding a pathological cell and which comprises an antibody constant region of the present invention may be produced according to standard art recombinant protein production methodology (for guidance, refer, for example, to the list of references provided in the introductory paragraph to the Examples section which follows) for producing such chimeric immunoglobulins, which may be referred to as "immunoadhesins" or "Fc fusion proteins" in the art.

It will be appreciated that decreasing the activity/level of the polypeptide, and increasing the association of complement with the pathological cells so as to achieve effective and specific complement-mediated cytolysis of the pathological cells may be achieved using a bispecific antibody specific for the polypeptide and specific for the pathological cells. Bispecific antibodies are well known and routinely employed in the art, and may easily be produced by one of ordinary skill in the art.

Preferably, an antibody or antibody fragment of the present invention specifically binds at least one epitope of a target antigen. As used herein, the term "epitope" refers to any antigenic determinant on an antigen to which the antibody specifically binds.

Epitopic determinants usually consist of chemically active surface groupings of molecules such as amino acids or carbohydrate side chains and usually have specific three dimensional structural characteristics, as well as specific charge characteristics.

As used herein, the term "antibody" refers to a substantially intact antibody molecule.

As used herein, the phrase "antibody fragment" refers to a functional fragment of an antibody that is capable of binding to a target antigen.

Suitable antibody fragments capable of specifically binding a target antigen include an Fv, a single chain Fv, an Fab, an Fab', and an F(ab')$_2$.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker.

(iii) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and $C_H1$ domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); and (v) F(ab')$_2$, a fragment of an antibody molecule containing a monovalent antigen-binding portion of an antibody molecule which can be obtained by treating whole antibody with the enzyme pepsin (i.e., a dimer of Fab' fragments held together by two disulfide bonds).

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U. S. A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote RJ. et al., 1983. Proc. Natl. Acad. Sci. U. S. A. 80:2026-2030; Cole SP. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumin (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in E. coli or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be crosslinked by chemicals such as glutaraldehyde.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Antibodies or antibody fragments may be fused using standard recombinant technology so as to generate bispecific antibodies having dual specificity. For guidance regarding suitable production and use of bispecific antibodies, refer for example, to: Kipriyanov SM, Le Gall F. et al., 2004. Recent advances in the generation of bispecific antibodies for tumor immunotherapy. Curr Opin Drug Discov Devel. 7:233-42; Peipp M, Valerius T., 2002. Bispecific antibodies targeting cancer cells. Biochem Soc Trans. 30:507-11; and Kriangkum J. et al., 2001. Bispecific and bifunctional single chain recombinant antibodies. Biomol Eng. 18:31-40.

It will be appreciated that for human therapy, humanized antibodies may be preferably used. Humanized forms of non human (e.g., murine) antibodies are genetically engineered chimeric antibodies or antibody fragments having-preferably minimal-portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boemer et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368:812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies are obtained, they may be tested for binding capacity, for example via ELISA, so as to determine suitable functional concentrations.

A compound used for decreasing the level/activity of the polypeptide in the pathological cell population of the present invention, and/or a compound for increasing the association of complement with the pathological cell population can be suitably formulated as a pharmaceutical composition which comprises a pharmaceutically acceptable carrier and which is suitably packaged as an article of manufacture.

Thus, according to this aspect of the present invention there is provided an article of manufacture which comprises packaging material and a pharmaceutical composition identified in print in or on the packaging material for treatment of the disease associated with the pathological cell population, where the pharmaceutical composition comprises a pharmaceutically acceptable carrier, and, as active ingredients a compound of the present invention for decreasing the level/activity of the polypeptide in the pathological cell population, and a compound of the present invention for increasing association of complement with the pathological cell population.

Thus, according to this aspect of the present invention there is further provided an article of manufacture which comprises packaging material and a pharmaceutical composition identified in print in or on the packaging material for treatment of the disease associated with the pathological cell population, where the pharmaceutical composition comprises a pharmaceutically acceptable carrier and, as one or more active ingredients the substantially cell membrane-impermeable compound, and, optionally, the compound for increasing the association of complement with the pathological cell population.

Ample guidance regarding suitable formulation of pharmaceutical compositions and their packaging as articles of manufacture is provided hereinbelow.

Thus, according to another aspect of the present invention there is provided a method of treating a disease associated with pathological complement-mediated cytotoxicity in a subject in need of treatment. The method is effected by increasing in a cell population affected by the cytotoxicity (hereinafter "affected cell population") the level/activity of the polypeptide.

As used herein, the term "increasing" when relating to the level/activity of the polypeptide refers to inducing, stimulating, promoting, increasing and/or upregulating the level/activity.

As used herein, the term "pathological" when relating to pathological complement-mediated cytotoxicity refers to a complement-mediated cytotoxicity whose elimination in a subject of the present invention having a disease associated with such cytotoxicity can be used to treat the disease in the subject.

As used herein, the term "cytotoxicity", when relating to complement-mediated cytotoxicity, refers to any process of cell/tissue damaging, killing and/or inflammation involving, or mediated by, any complement protein, or any complex of complement proteins, including complement membrane attack complex (MAC)/C5b-9, which is capable of facilitating cytolysis and/or inflammatory damage/killing of cells/tissue, and including C3, C4 and/or C5 fragments, which can facilitate inflammatory damage/killing of cells/tissue.

The method according to this aspect of the present invention, by virtue of enabling increasing of vesicular shedding of complement by a pathological cell population, and enabling decreasing of complement-mediated cytotoxicity in a pathological cell population, can be used to treat any of various diseases associated with pathological complement-mediated cytotoxicity, including autoimmune, immune-complex and transplantation-related diseases. It will be appreciated that an autoantibody-mediated autoimmune disease is associated with a cell population affected by complement-mediated cytotoxicity induced by such autoantibodies, that a disease associated with pathological immune complex deposition (immune complex disease) is associated with a cell population affected by complement-mediated cytotoxicity induced by such immune complex deposition, and that a transplantation-related disease such as graft rejection mediated by anti-graft antibodies is associated with graft cells affected by complement-mediated cytotoxicity induced by such anti-graft antibodies. As such, it will be appreciated that the method according to this aspect of the present invention can be used to treat such diseases by decreasing cytotoxicity mediated by such pathological antibodies in such affected cells, in accordance with the teachings of the present invention, as described further hereinbelow.

Increasing the level/activity of the polypeptide in the affected cell population can be achieved in any of various ways.

Preferably, increasing the level/activity of the polypeptide in the pathological cell population is effected so as to maximally increase the level/activity of the polypeptide in the pathological cell population, so as to optimally decrease complement-mediated cytotoxicity in the affected cell population, to thereby achieve optimal disease treatment.

Increasing the level/activity of the polypeptide in the affected cell population is preferably effected by a method which comprises administering to the subject an exogenous polynucleotide designed and constructed to express at least a functional portion of the polypeptide in the affected cell population, and/or by a method which comprises administering to the subject a molecule capable of activating the polypeptide.

As is described and illustrated in the Examples section which follows, genetically modifying a cell population affected by complement-mediated cytotoxicity to express a polypeptide of the present invention such as mortalin can be used to effectively decrease such cytotoxicity in such affected cells (refer, for example, to FIG. 9).

Alternately, increasing the level/activity of the polypeptide in the affected cell population may be effected by a method which comprises administering to the subject a compound capable of increasing an expression of an endogenous DNA or mRNA encoding the polypeptide.

It will be well within the purview of one of ordinary skill in the art to suitably increase the level/activity of a polypeptide of the present invention in an affected cell population of the present invention via any one of various commonly practiced prior art methods.

Increasing the level/activity of the polypeptide in the affected cell population by administering to the subject an exogenous polynucleotide may be effected whereby the exogenous polynucleotide is a DNA or RNA. Depending on the application and purpose, the polynucleotide may be administered directly to the subject or it may be administered to the subject in the form of cells which have been genetically modified with the polynucleotide in such a way as to enable delivery of the construct to the affected cell population in-vivo.

Coding sequence information for expression of a polypeptide of the present invention such as human mortalin is available from several databases including the GenBank database available through ncbidotnlmdotnihdotgov/. To express the exogenous polynucleotide in the affected cell population, a DNA encoding a polypeptide of the present invention, such as human mortalin (Gene, HSPA9B; DNA sequence, GenBank Accession number NM_004134) is preferably ligated into a nucleic acid construct suitable for mammalian cell expression.

The nucleic acid construct includes a promoter sequence for directing transcription of the polynucleotide sequence in the affected cells in a constitutive or inducible manner. Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") may advantageously include additional sequences which render this vector suitable for replication and integration in prokaryotes, eukaryotes, or preferably both (e.g., shuttle vectors). In addition, a typical cloning vector may also contain a transcription and translation initiation sequence, a transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, for example: Enhancers and Eukaryotic Expression, Cold Spring Harbor Press, Cold Spring Harbor, N.Y. 1983.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

The vector may include a eukaryotic replicon to enable vector amplification in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

If necessary, the expression vector can include nucleotide sequences that allow translation of several proteins from a single mRNA such as an internal ribosome entry site (IRES) and sequences for genomic integration of the promoter-chimeric polypeptide.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viral vectors have the capacity to specifically target predetermined cell types and thereby introduce a recombinant gene into the infected cell. Thus, a suitable viral vector may be selected to transform cells of a specific lineage. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang CY et al., 2004 (Arch Virol. 149: 51-60).

Recombinant viral vectors are useful for in vivo expression of a polypeptide of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Another suitable expression vector may be an adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues and easy production of high titers [Russel, W. C. [J. Gen. Virol. 81: 57-63 (2000)]. The adenovirus DNA is transported to the nucleus, but does not integrate thereinto. Thus the risk of mutagenesis with adenoviral vectors is minimized. Adenoviral vectors used in experimental cancer treatments are described by Seth et al. [Adenoviral vectors for cancer gene therapy. In: P. Seth (ed.) Adenoviruses: Basic biology to Gene Therapy, Landes, Austin, Tex., (1999) pp. 103-120].

A suitable viral expression vector may also be a chimeric adenovirus/retrovirus vector which combines retroviral and adenoviral components. Such vectors may be more efficient than traditional expression vectors for transducing tumor cells [Pan et al., Cancer Letters 184: 179-188 (2002)].

Various methods can be used to introduce the expression vector into an affected cell population of the present invention. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Genetic modification of cells by viral infection offers several advantages over other methods such as lipofection and electroporation, since higher transfection efficiency can be obtained due to the infectious nature of viruses.

As described hereinabove, increasing the level/activity of the polypeptide in the affected cell population may be effected by a method which comprises administering to the subject a molecule capable of activating the polypeptide.

Examples of molecules capable of activating the polypeptide include cathepsin inhibitors, such as the cathepsin L inhibitor Z-Phe-Phe-CH2F. As is described and illustrated in the Examples section which follows (refer, for example, to FIGS. 8a-b), treating a cell population affected by pathological complement-mediated cytotoxicity can be used to increase cellular levels of a polypeptide of the present invention such as mortalin, and to concomitantly decrease the cytotoxicity in the affected cell population.

A compound used for increasing the level/activity of the polypeptide in the pathological cell population of the present invention can be suitably formulated as a pharmaceutical composition which comprises a pharmaceutically acceptable carrier and which is suitably packaged as an article of manufacture.

Thus, according to this aspect of the present invention there is provided an article of manufacture which comprises packaging material and a pharmaceutical composition identified in print in or on the packaging material for treatment of a the disease associated with pathological complement-mediated cytotoxicity, where the pharmaceutical composition comprises a pharmaceutically acceptable carrier and, as an active ingredient, the compound for increasing in the affected cell population of the subject the level/activity of the polypeptide.

One of ordinary skill in the art, such as a physician, preferably a physician specialized in the disease to be treated, will possess the necessary expertise for adapting the teachings of the present invention for suitably treating a disease of the present invention in a given subject. In particular, one of ordinary skill in the art will possess the necessary expertise for selecting a suitable administration route for administering a therapeutic compound of the present invention, will possess the necessary expertise for selecting a suitable dosage and frequency of administration for administering a therapeutic compound of the present invention, and will possess the necessary expertise for suitably monitoring the disease so as to achieve a desired therapeutic outcome.

Suitable routes of administration of a therapeutic compound of the present invention are described hereinabove.

As is described in the Examples section which follows, exposure of pathological cells, such as cancer cells, to a 1:40 to 1:30 dilution of rabbit polyclonal antiserum specific for a polypeptide of the present invention such as mortalin can be used to facilitate complement-mediated cytolysis of the cells. Since such antiserum will generally contain about 10-15 milligrams per milliliter of total antibody, of which about 2-3 percent is specific for the antigen, administration to the subject of an antibody specific for the polypeptide when treating the disease associated with the pathological cell population according to the teachings of the present invention may be suitably effected by administering to the subject a dose of the antibody so as to expose the pathological cells to a therapeutic concentration of the antibody selected from a range of about 5 micrograms/ml to about 15 micrograms/ml, such as a concentration of about 10 micrograms/ml. The concentration may be selected, for example, from a range of about 1 microgram/ml to about 100 micrograms/ml. It will be appreciated that the concentration of the antibody should be appropriately adjusted according to the binding affinity of the antibody employed for the pathological cell population associated with the disease being treated. For example, treatment of a circulating hematopoietic malignancy may be effected by administering the antibody so as to achieve a serum concentration thereof corresponding to a suitable therapeutic concentration. As used herein, the qualifier "about" denotes a variation of plus/minus 10 percent.

Guidance for suitable administration of antibodies specific for pathological cells, such as antibodies specific for tumor-associated antigens, for treatment of diseases associated with such pathological cells, such as tumors, according to the teachings of the present invention is widely available in the art (refer, for example, to Harris M., 2004. Monoclonal antibodies as therapeutic agents for cancer. Lancet Oncol. 5:292-302; Curtis MA., 2003. New monoclonal antibodies for hematologic malignancies (and breast cancer). Med Health R I. 86:256-7; Houshmand P, Zlotnik A., 2003. Targeting tumor cells. Curr Opin Cell Biol. 15:640-4).

A therapeutic compound of the present invention may be suitably administered over any one of various durations; and may be suitably administered continuously, or discontinuously in order to achieve disease treatment.

For treating a disease associated with a pathological cell population such as a tumoral disease, increasing the association of complement with the pathological tumor cell population so as to therapeutically increase complement-mediated cytolysis thereof may be optimally effected by administering to the subject an antibody capable of specifically binding an antigen which is specifically displayed by the tumor cell population. In the case of a malignant tumor, such antigens are commonly referred to as tumor-associated antigens, and characterization and identification of such antigens is routinely practiced in the art, for example during diagnosis and staging of the disease. Antibodies specific for such antigens which may be used to treat a disease of the present invention include, for example, Rituxan (rituximab) commonly used for treatment of relapsed or refractory CD20-positive non-Hodgkin's B-cell lymphoma; and Herceptin (trastuzumab) commonly employed for treatment of mammary tumors overexpressing the human epidermal growth factor receptor 2 (HER-2).

While various tumor specific antibodies have been developed for cancer therapy, their in-vivo efficiency in complement activation is poor, and, as such, the present invention can be used to enhance complement-mediated cytolysis of tumors cells induced by such antibodies, thereby improving cancer treatment via such antibodies.

For treating a disease associated with a pathological cell population such as an intracellular pathogen infection, increasing the association of complement with the pathological infected cell population so as to therapeutically increase complement-mediated cytolysis thereof may be optimally effected by administering to the subject an antibody capable of specifically binding an antigen of the pathogen displayed on the surface of the infected cell population. Such antigens include those which are displayed complexed with an MHC molecule. Antibodies specific for such MHC-antigen complexes are well known in the art.

For treating a disease associated with a pathological cell population such as an autoimmune disease mediated by pathogenic autoantigen specific T-cells or B-cells/antibodies, increasing the association of complement with the pathological lymphocyte population so as to therapeutically increase complement-mediated cytolysis thereof may be optimally effected by administering to the subject an antibody capable of specifically binding an autoantigen-specific T-cell or B-cell antigen receptor of the pathological T-lymphocyte or B-lymphocyte population, respectively.

Similarly, for treating transplantation-related diseases, antibodies specific for T- or B-cell receptors can be used to increase complement-mediated cytotoxicity of pathological T- or B-cells, respectively, so as to therapeutically increase complement-mediated cytolysis of such pathological lymphocytes. For example, such treatment of allograft rejection may be achieved using antibodies specific for T-cell receptors of the pathological allograft-reactive T-cell population; such treatment of xenograft rejection according to the present invention may be achieved using antibodies specific for B-cell receptors of the pathological xenograft-reactive B-cell population; and such treatment of graft-versus-host disease (GVHD) according to the present invention may be achieved using antibodies specific for T- or B-cell receptors, as suitable, of the pathological host-reactive T- or B-cell population.

Antibodies specific for T-cell or B-cell receptors, commonly termed "anti-idiotype" antibodies, are well known and routinely employed in the art.

It will be appreciated that antibodies specific for any one of various antigens other than lymphocyte receptors, which are specifically displayed at the surface of pathogenic lymphocyte populations in subjects having a transplantation-related disease may also be used to induce cytolysis of such lymphocyte populations so as to achieve disease treatment according to the teachings of the present invention. Such antigens may be, for example allelic variants specifically expressed in the graft recipient but not in the graft, or vice-versa.

It will be further appreciated that the teaching of the present invention whereby antibodies specific for polypeptides of the present invention such as mortalin can be used to increase complement-mediated cytolysis of pathological cells, and hence can be used to treat diseases associated with such cells, is clearly novel and non-obvious over the prior art. This is clearly the case since the prior teaches, for example: that anti-mortalin antibodies block immune cytolysis of cancer cells (Kim, H. T. et al., 1995. J Immunol 154:1614); that members of the hsp70 family and related chaperones are known to be involved in peptide binding and antigen presentation and may be used for treatment of cancer and infection (Castelli, C. et al., 2004. Cancer Immunol Immunother 53:227; Srivastava, P. 2002. Annu Rev Immunol 20:395); and that HSP70 is a potent activator of the complement system (Prohaszka Z. et al., 2002. Heat shock protein 70 is a potent activator of the human complement system. Cell Stress Chaperones. 7:17-22). As such, the prior art clearly teaches against the presently taught use of negatively regulating levels/activity of mortalin, which is an HSP70 family member, to treat diseases associated with pathological cells.

Examples of types and specific examples of diseases treatable according to the method of the present invention are listed hereinbelow.

Types of tumoral diseases amenable to treatment via the method of the present invention include benign tumors, warts, polyps, precancers, and malignant tumors/cancer.

Specific examples of tumoral diseases which can be treated using the method of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma; lung cancer; lung cancer, small cell; lymphoma, non-Hodgkin's; lynch cancer family syndrome II; male germ cell tumor; mast cell leukemia; medullary thyroid; medulloblastoma; melanoma; meningioma; multiple endocrine neoplasia; myeloid malignancy, predisposition to; myxosarcoma; neuroblastoma; osteosarcoma; ovarian cancer; ovarian cancer, serous; ovarian carcinoma; ovarian sex cord tumors; pancreatic cancer; pancreatic endocrine tumors; paraganglioma, familial non-chromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the present invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

Preferably, the tumoral disease is a malignant tumor, more preferably a malignant hematopoietic malignancy, more preferably a leukemia, and most preferably an erythroleukemia. As is described and illustrated in the Examples section which follows, the method of the present invention can be used to increase complement-mediated cytolysis of human erythroleukemia cells (refer, for example, to FIGS. 5a-b).

Specific examples of intracellular pathogens infections which may be treated according to the teachings of the present invention include, but are not limited to, infections by viral pathogens, intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picomaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, *Herpes simplex* virus infection, yellow fever, Ebola virus infection, rabies, etc.

Specific examples of transplantation-related diseases which may be treated according to the teachings of the present invention include but are not limited to graft rejection, chronic graft rejection, subacute graft rejection, hyperacute graft rejection, acute graft rejection, allograft rejection, xenograft rejection and graft-versus-host disease (GVHD).

Specific examples of antibody-mediated autoimmune diseases which may be treated according to the teachings of the present invention include, but are not limited to, rheumatoid diseases, rheumatoid autoimmune diseases, rheumatoid arthritis (Krenn V. et al., Histol Histopathol 2000 July;15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998;17 (1-2):49), sclerosis, systemic sclerosis (Renaudineau Y. et al., Clin Diagn Lab Immunol. 1999 March;6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October;34 Suppl:S125), thyroid diseases, autoimmune thyroid diseases, Graves' disease (Orgiazzi J. Endocrinol Metab Clin North Am 2000 June;29 (2):339), thyroiditis, spontaneous autoimmune thyroiditis (Braley-Mullen H. and Yu S, J Immunol 2000 December 15;165 (12):7262), Hashimoto's thyroiditis (Toyoda N. et al., Nippon Rinsho 1999 August;57 (8):1810), myxedema, idiopathic myxedema (Mitsuma T. Nippon Rinsho. 1999 August;57 (8):1759); autoimmune reproductive diseases, ovarian diseases, ovarian autoimmunity (Garza K M. et al., J Reprod Immunol 1998 February;37 (2):87), autoimmune anti-sperm infertility (Diekman A B. et al., Am J Reprod Immunol. 2000 March;43 (3):134), repeated fetal loss (Tincani A. et al., Lupus 1998;7 Suppl 2:S107-9), neurodegenerative diseases, neurological diseases, neurological autoimmune diseases, multiple sclerosis (Cross A H. et al., J Neuroimmunol 2001 January 1;112 (1-2):1), Alzheimer's disease (Oron L. et al., J Neural Transm Suppl. 1997;49:77), myasthenia gravis (Infante AJ. And Kraig E, Int Rev Immunol 1999;18 (1-2):83), motor neuropathies (Komberg A J. J Clin Neurosci. 2000 May;7 (3):191), Guillain-Barre syndrome, neuropathies and autoimmune neuropathies (Kusunoki S. Am J Med Sci. 2000 April;319 (4):234), myasthenic diseases, Lambert-Eaton myasthenic syndrome (Takamori M. Am J Med Sci. 2000 April;319 (4): 204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January;156 (1):23); neuropathies, dysimmune neuropathies (Nobile-Orazio E. et al., Electroencephalogr Clin Neurophysiol Suppl 1999;50:419); neuromyotonia, acquired neuromyotonia, arthrogryposis multiplex congenita (Vincent A. et al., Ann N Y Acad Sci. 1998 May 13;841 :482), cardiovascular diseases, cardiovascular autoimmune diseases, atherosclerosis (Matsuura E. et al., Lupus. 1998;7 Suppl 2:S135), myocardial infarction (Vaarala O. Lupus. 1998;7 Suppl 2:S132), thrombosis (Tincani A. et al., Lupus 1998;7 Suppl 2:S107-9), granulomatosis, Wegener's granulomatosis, arteritis, Takayasu's arteritis and Kawasaki syndrome (Praprotnik S. et al., Wien Klin Wochenschr 2000 August 25;112 (15-16):660); anti-factor VIII autoimmune disease (Lacroix-Desmazes S. et al., Semin Thromb Hemost.2000;26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May;151 (3):178); antiphospholipid syndrome (Flamholz R. et al., J Clin Apheresis 1999;14 (4):171); heart failure, agonist-like beta-adrenoceptor antibodies in heart failure (Wallukat G. et al., Am J Cardiol. 1999 June 17;83 (12A):75H), thrombocytopenic purpura (Moccia F. Ann Ital Med Int. 1999 April-June;14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January;23 (1):16), celiac disease (Landau Y E. and Shoenfeld Y. Harefuah 2000 January 16;138 (2):122), autoimmune diseases of the musculature, myositis, autoimmune myositis, Sjogren's syndrome (Feist E. et al., Int Arch Allergy Immunol 2000 September;123 (1):92); smooth muscle autoimmune disease (Zauli D. et al., Biomed Pharmacother 1999 June;53 (5-6):234), hepatic diseases, hepatic autoimmune diseases, autoimmune hepatitis (Manns M P. J Hepatol 2000 August;33 (2):326) and primary biliary cirrhosis (Strassburg C P. et al., Eur J Gastroenterol Hepatol. 1999 June;11 (6):595).

Specific examples of immune complex diseases which may be treated according to the teachings of the present invention include, but are not limited to: amyloid plaque diseases, such as Alzheimer disease (Stoltzner S E. et al., 2000. Temporal accrual of complement proteins in amyloid plaques in Down's syndrome with Alzheimer's disease. Am J Pathol. 156:489-99); chronic allograft rejection (Conti F. et al., 1997. Expression of the membrane attack complex of complement and its inhibitors during human liver allograft transplantation. J Hepatol. 27:881-9); diabetic neuropathy (Rosoklija G B. et al., 2000. Local activation of the complement system in endoneurial microvessels of diabetic neuropathy. Acta Neuropathol (Berl). 99:55-62); glomerulonephritis; intracerebral hemorrhage (Hua Y. et al., 2000. J Neurosurg. 92:1016-22); multiple sclerosis (Scolding N J. et al., 1998. J Neuroimmunol. 84:69-75); myasthenia gravis (Lang T J. et al., 1997. J Neurochem. 68:1581-9); myocardial infarction (Silkensen J R. et al., 1998. J Lab Clin Med. 131: 28-35); X-linked vacuolated myopathy (Louboutin J P. et al., 1998. X-linked vacuolated myopathy: membrane attack complex deposition on the surface membrane of injured muscle fibers is not accompanied by S-protein. Muscle Nerve. 21:932-5); and xenograft rejection (Gralinski M R. et al., 1996. Am J Physiol. 271:H571-8).

As described hereinabove, the present invention provides articles of manufacture which comprise packaging material and pharmaceutical compositions for treatment of diseases of the present invention.

As used herein a "pharmaceutical composition" refers to a preparation of one or more of the active ingredients described herein with other chemical components such as physiologically suitable carriers and excipients. The purpose of the pharmaceutical composition is to facilitate administration of the active ingredients to the subject.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, PA, latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of the subject.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Thus, the present invention provides novel and optimal methods of, and articles of manufacture for, treating, via modulation of levels/activity of HSP70 family proteins, diseases associated with pathological cells and treatable via complement-mediated cytolysis of such pathological cells and/or associated with pathological complement-mediated cytotoxicity, such as tumoral, infectious, transplantation-related, autoimmune, and immune complex deposition-mediated diseases.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Effective Modulation of Complement-mediated Cytolysis via Regulation of Mortalin Activity/Levels: Novel and Optimal Disease Treatment Method Introduction: Diseases associated with pathological complement-mediated cytotoxicity, such as autoimmune, immune-complex and transplantation-related diseases represent numerous highly debilitating and/or lethal diseases for which no optimal therapy exists. Similarly, diseases associated with pathological cells, such as tumoral, infectious, autoimmune and transplantation-related diseases, which are amenable to treatment via complement-mediated cytolysis of such pathological cells, also represent numerous highly debilitating and/or lethal diseases for which no optimal therapy exists. Complement-mediated cytotoxicity has been suggested to be regulated by proteins of the 70 kDa heat-shock protein (HSP70) family, and, as such, an optimal strategy for treating the aforementioned diseases may be via appropriate regulation of activity/levels of HSP70 family proteins. While various approaches involving regulation of activity/levels of HSP70 family proteins for treatment of such diseases have been proposed, these are associated with critical disadvantages, including never having demonstrated any, or any satisfactory therapeutic capacity. While reducing the present invention to practice, as described below, a novel and effective means of exploiting regulation of activity/levels of an HSP70 family protein so as to regulate complement-mediated cytotoxicity so as to enable disease treatment was unexpectedly uncovered, thereby overcoming the limitations of the prior art.

Materials and Methods:

Cells and cell lysates: The human erythroleukemic cell line K562 was cultured in RPMI-1640 medium supplemented with 10 percent (v/v) heat-inactivated fetal bovine serum (Gibco laboratories, Grand Island, NY, USA), 1 percent glutamine, 2 percent pyruvate and antibiotics mixture (Bio-Lab, Jerusalem, Israel), at 37 degrees centigrade in a 5 percent carbon dioxide atmosphere. To prepare cell lysates, 20 million cells were mixed with 1 milliliter lysis buffer composed of 100 millimolar Tris-pH 7.5, 10 millimolar EDTA, protease inhibitor cocktail (Sigma) and 0.7 percent Triton X-100. After 3 cycles of freezing and thawing, the cell lysate was subjected to centrifugation for 15 minutes at 14,000×g, and the supernatant was collected and diluted with 1 milliliter HBSS (Sigma, Rehovot, Israel).

Sera, antisera and reagents: Normal human serum (NHS) was prepared from healthy individuals. Heat inactivation of NHS was performed by incubation at 56 degrees centigrade for 30 minutes. C7- or C8-depleted human sera were prepared from C7- or C8-deficient patients, respectively, as previously described (Schlesinger, M. et al., 1990. Clin Exp Immunol 81:423). Human sera were kept frozen at minus 70 degrees centigrade in small aliquots and thawed only once. Purified human C8 protein was purchased from Advanced Research Technologies (San Diego, Calif., USA). A polyclonal antiserum directed to K562 cells was prepared in rabbits or mice. Rabbit anti-mortalin antibodies were kindly provided by Dr. Sunil Kaul (AIT, Tsukuba Ibaraki, Japan; Wadhwa, R. et al., 1993. J Biol Chem 268:6615) and Dr. Alex Merrick (NIEHS, Research Triangle, N.C., USA; Merrick, B. A. et al., 1997. Cancer Lett 119:185). Peroxidase-conjugated goat anti-rabbit IgG, streptolysin O (SLO), mellitin and HEPES were purchased from Sigma. The pharmacological inhibitors PD98059, GF109203X and polymyxin B were obtained from Calbiochem (San Diego, Calif., USA).

Cell lysis and induced protection assays: Cytotoxicity assays were performed as previously described (Reiter, Y. and Fishelson, Z. 1992. Mol Immunol 29:771). Briefly, cells were incubated with diluted anti-K562 antiserum for 30 minutes at 4 degrees centigrade and then with complement (NHS, C7- or C8-deficient serum or HI-NHS, 50 percent) for 60 minutes at 37 degrees centigrade. Cell lysis was determined via Trypan blue staining. For the complement-induced protection assays, the cells were first treated with sublytic doses of antibody and NHS, washed and then incubated with lytic doses of antibody and NHS (Reiter, Y. et al., 1992. Eur J Immunol 22:1207). Statistical significance was analyzed by using the two-sided unpaired student's t-test.

Collection of extracellular protein: Cells were treated with antibodies for 30 minutes at 4 degrees centigrade and then with NHS or HI-NHS (50 percent) for 10 minutes at 37 degrees centigrade. Then, the cells were extensively washed into HBSS and incubated at 37 degrees centigrade. At different times, cells were removed by centrifugation at 250×g and supernatants were collected and kept frozen until analyzed. In some experiments, cells were first metabolically labeled for 2 hours at 37 degrees centigrade with an L-[$^{35}$S]methionine, L-[$^{35}$S]cysteine mix (Amersham Pharmacia, Uppsala, Sweden) at 200 microcuries per milliliter in RPMI (lacking methionine and cysteine) and 20 millimolar HEPES-pH 7.0. Cytotoxicity assays and collection of extracellular proteins were performed as described above. Radioactivity in the supernatants was quantified in a beta-Scintillation Counter (Tri-Carb, Packard).

Protein analyses: Protein concentration was analyzed with the BCA Protein Assay Kit (Pierce, Rockford, Ill., USA). Samples of 20 micrograms of protein was subjected to SDS-PAGE under reducing conditions (50 millimolar DTT), in a 10 percent acrylamide gel, and stained with Coomassie Blue or silver. Selected protein species were excised from Coomassie Blue-stained gels and analyzed by mass spectrometry (MALDI-MS) at the Maiman Institute for Proteome Research (Tel-Aviv University). Alternatively, the electrophoretically separated proteins were transferred onto a nitrocellulose membrane (Schleicher & Schuell, Dassel, Germany). The membrane was blocked with 5 percent skim milk (Tnuva, Rehovot, Israel) in Tris-buffered saline containing 0.05 percent Tween-20 (Sigma; TBST) for 1 hour at room temperature. The membrane was treated with rabbit anti-mortalin antibodies and then with peroxidase-conjugated goat anti-rabbit IgG. The labeled membrane was developed with an enhanced chemiluminescence reagent (Pierce, Rockford, Ill., USA) and exposed to a SuperRX film (Fuji, Tokyo, Japan).

Binding of mortalin to complement C9: Purified human C9 (Advanced Research Technologies, San Diego, Calif.) and BSA (Sigma; 1 microgram each) were subjected to SDS-PAGE under reducing conditions (50 millimolar DTT), in a 10 percent acrylamide gel and transferred onto a nitrocellulose membrane. The membrane was then incubated for 2 hours at 37 degrees centigrade with K562 cell lysates supplemented or not with 2 micrograms human C9. After two washes with TBST, Western blotting analysis was performed, as described above, with anti-mortalin antibody.

Figure 2A:
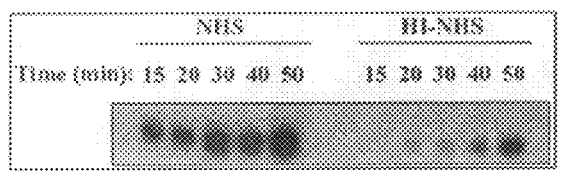
FIGS. 2a-e are Western immunoblotting assay data depicting that mortalin is maximally released following sublytic complement attack, and is released by viable, as opposed to damaged, cells. K562 cells were treated with a sublytic dose of anti-K562 antibody and NHS or HI-NHS. After 10 minutes at 37 degrees centigrade the cells were washed and incubated at 37 degrees centigrade. At different times, the supernatants (FIG. 2a) and cells (FIG. 2b) were separated and analyzed each by SDS-PAGE and Western blotting with rabbit anti-mortalin antibody.
Figure 2B:
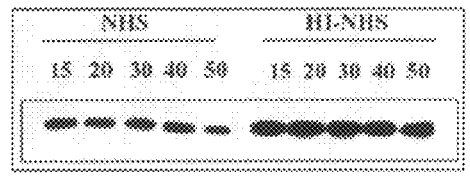
Figure 2C:
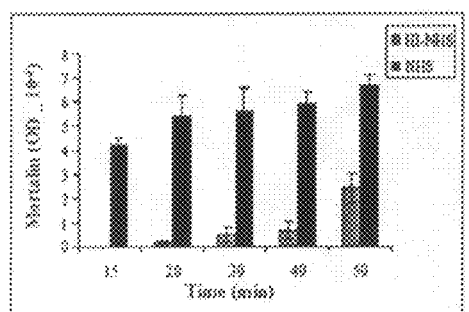
Figure 2D:
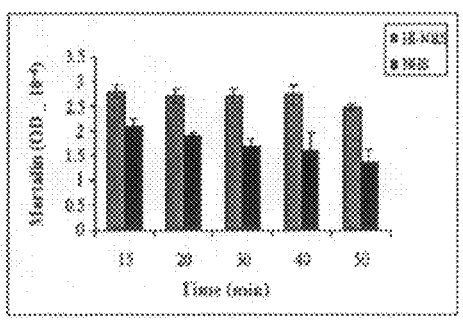
Figure 2E:
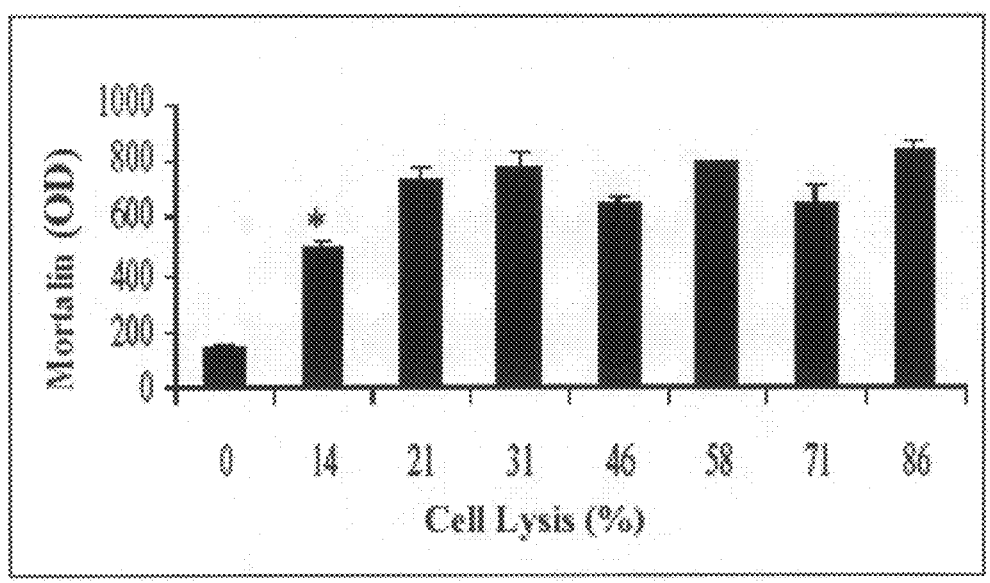

Experimental Results:

Release of mortalin following a sublytic complement attack: Proteins are spontaneously released from cells cultured at 37 degrees centigrade. Protein release is elevated following exposure of cells to a sublytic dose of antibody and NHS (data not shown). In order to find qualitative differences between protein profiles of supernatants collected from cells treated with complement (NHS) or control cells (HI-NHS), supernatants were analyzed by SDS-PAGE and stained with silver or Coomassie Blue (FIG. 1a). A protein species having a molecular weight of approximately 75 kDa was found in NHS-treated cells but was poorly visible in control cells. To identify this protein, it was excised after Coomassie Blue staining from the gel and subjected to MALDI-MS analysis (FIG. 1b). Seven different peptides identified in the MS analysis, gave complete matching with mortalin (mot-2, GRP75; gene: HSPA9B; GenBank Identifier gi:24234688; SEQ ID NO: 1). The kinetics of the mortalin release were studied next. Supernatants were collected from K562 cells at different times following treatment with sublytic NHS or with HI-NHS, and were analyzed by Western Blotting (FIGS. 2a-b). A significant level of extracellular mortalin was found in supernatants collected 15 minutes following treatment with complement and the amount of mortalin kept slightly rising up until 60 minutes. In contrast, the spontaneous release of mortalin in control cells was very low. Concomitantly, the intracellular level of mortalin gradually decreased from 15 to 60 minutes (FIGS. 2c-d). In contrast, the concentration of mortalin within control cells was stable. To rule out the possibility that mortalin leaks out of dead cells, the amount of released mortalin as a function of level of cell damage was verified. Cells were treated with increasing concentrations of antibodies and 50 percent NHS. Percent cell lysis increased from 0 to 86 percent (FIG. 2e). Next, the quantity of extracellular mortalin was assessed on Western blots. As shown in FIG. 2e, the most significant increase in mortalin release occurred under sublytic conditions (14-21 percent lysis). At higher, lytic conditions, there was no additional increase in amount of extracellular mortalin. These findings indicate that mortalin is released from intact and not from damaged cells.

Figure 3B:
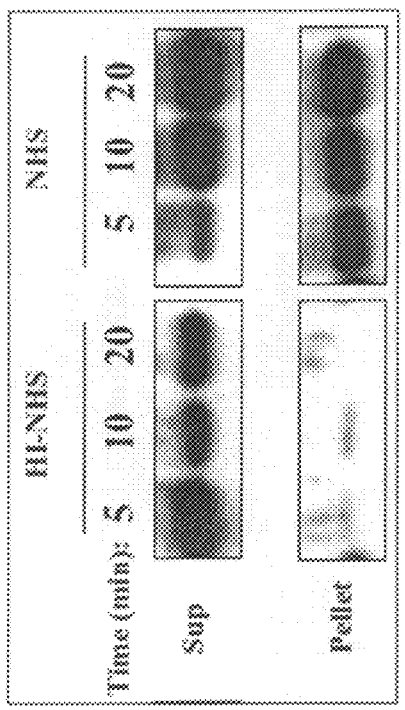
FIGS. 3a-d are a set of Western immunoblotting assay photographs depicting that mortalin and C9 are released in membrane vesicles. K562 cells treated with a sublytic doses of antibody and NHS or HI-NHS for 10 minutes at 37 degrees centigrade were washed into HBSS, incubated at 37 degrees centigrade and supernatants were collected after 5, 10 and 20 minutes. Released proteins were sedimented at 100,000×g and supernatants (Sup) and pellets were analyzed by SDS-PAGE and Western blotting with anti-mortalin (FIG. 3a) or anti-C9 (FIG. 3b) antibodies.
Figure 3D:
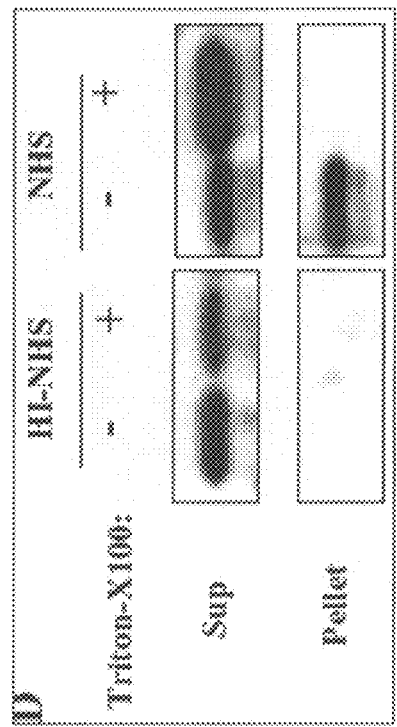
Figure 3A:
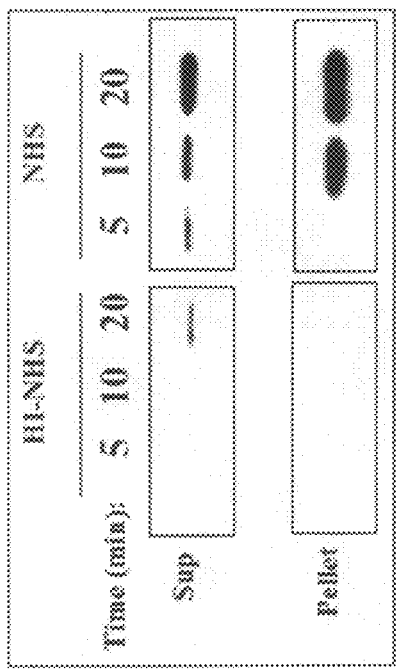
Figure 3C:
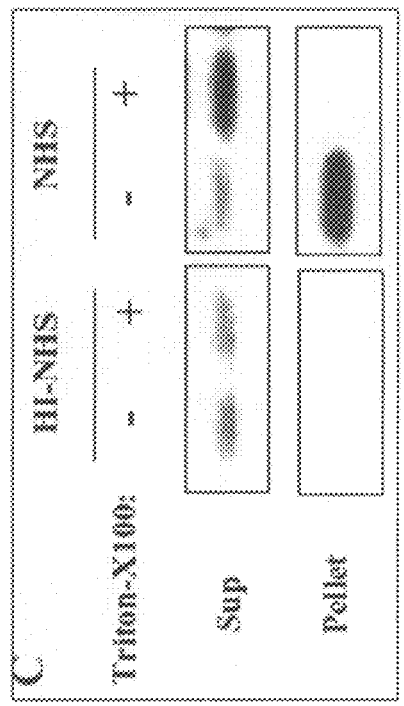

Indications that mortalin is associated with membrane vesicles: Supernatants collected from K562 cells treated with sublytic NHS or HI-NHS were sedimented at 5,000×g to remove cell debris. The supernatants were then subjected to centrifugation at 100,000×g, conditions known to pellet small membrane vesicles, and the resultant pellet and supernatant were subjected to SDS-PAGE and Western blotting. analysis with anti-mortalin antibodies (FIG. 3a) or with anti-C9 antibodies (FIG. 3b), indicated that both mortalin and C9 released from K562 cells treated with sublytic complement could be pelleted at 100,000×g. Pre-treatment of the supernatants with 0.1 percent Triton-X100, prior to the high-speed centrifugation, resulted in translocation of both mortalin and C9 from the pellet to the supernatant (FIGS. 3c-d), probably due to solubilization of the membrane vesicles bearing mortalin and C9.

Figure 4A:
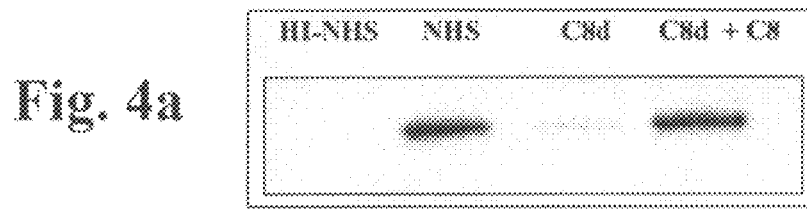
FIGS. 4a-d are Western immunoblotting assay data depicting that mortalin secretion is induced by complement complex C5b-9 and not by mellitin and SLO.
Figure 4B:
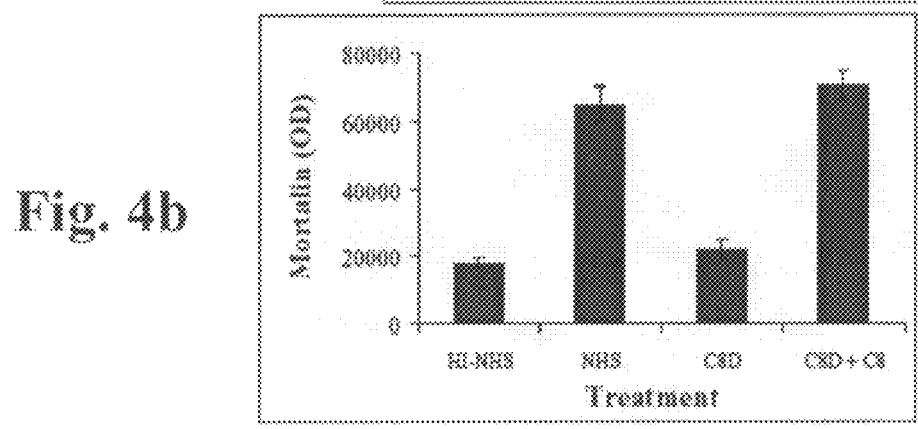

Mortalin release depends on complement complex C5b-9: In the absence of C8, the terminal complement complex is composed only of C5b-7 (Muller-Eberhard, H. J. 1986. Annu Rev Immunol 4:503). To determine whether complement complex C5b-9 is essential for release of mortalin, the effect of NHS was compared with that of a C8-deficient human serum. Supernatants were collected from K562 cells treated with antibody and C8-deficient serum or NHS and analyzed by Western blotting for mortalin binding (FIGS. 4a-b). Unlike NHS, only a small amount of mortalin was released from cells treated with C8-deficient serum. Upon reconstitution of the C8-deficient serum with purified C8 (to 55 micrograms per milliliter final concentration), it caused as much mortalin release as NHS.

Figure 4C:
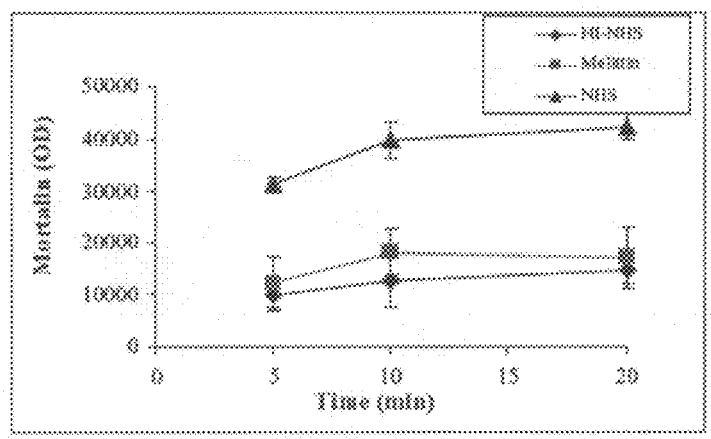
Figure 4D:
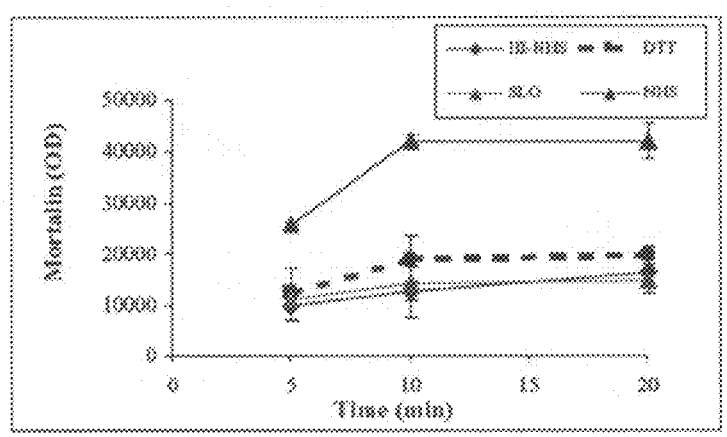

Streptolysin O (SLO) and mellitin are pore-forming proteins related to complement C9 (Laine, R. O. et al., 1988. Biochemistry 27:5308; Bhakdi, S. et al., 1985. Infect Immun 47:52; Reiter, Y. et al., 1995. J Immunol 155:2203). In order to find out whether release of mortalin is selectively induced by C5b-9 or can also be induced by other pore-formers, K562 cells were subjected to treatment with sublytic doses of mellitin or SLO. Analysis of supernatants collected from these cells clearly demonstrated that mortalin was not released in response to mellitin or SLO treatment (FIGS. 4c-d, respectively).

Anti-mortalin antibodies sensitize cells to complement-mediated lysis: To address the biological relevance of mortalin release, the effect of anti-mortalin antibodies on cell death induced by MAC was examined. K562 cells were treated with antibody and NHS in the presence of anti-mortalin antibodies or of prebleed serum as control. The anti-mortalin antibodies significantly increased complement-mediated lysis of K562 cells (FIG. 5a). In order to rule out the possibility that the anti-mortalin antibodies simply recruit more complement to the cell surface, the assay was performed in two stages. First, cells were treated with C8-deficient human serum (C8D) and washed, and then with anti-mortalin antibodies and C7-deficient-human serum (C7D) in presence of EDTA. In this case, the anti-mortalin antibodies were added to cells bearing C5b-7 complexes and could only block formation of C5b-8 and C5b-9 complexes. Again, prebleed serum served as control. In this experiment too, anti-mortalin antibodies increased sensitivity of K562 cells to lysis by complement (FIG. 5b).

Figure 6A:
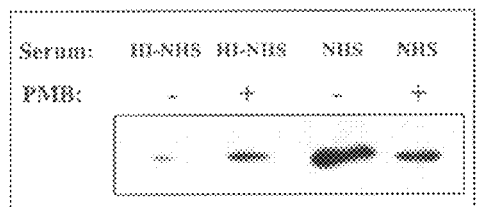
FIGS. 6a-g are pharmacological inhibition assay data depicting that PKC and ERK are involved in mortalin release. K562 cells were pretreated for 30 minutes at 37 degrees centigrade with 100 micrograms per milliliter polymyxin B (PMB) or PBS as control (FIGS. 6a-b) or with 10 micromolar PD98059 (PD) or 0.1 percent DMSO as control (FIGS. 6c-d). The cells were then treated with a sublytic dose of anti-K562 antibody and NHS or HI-NHS. After 10 minutes at 37 degrees centigrade, the cells were washed and incubated for 10 minutes at 37 degrees centigrade. Supernatants were collected and analyzed by SDS-PAGE and Western blotting with anti-mortalin antibodies. Densitometric analysis of 3 independent experiments is shown in B and D.
Figure 6C:
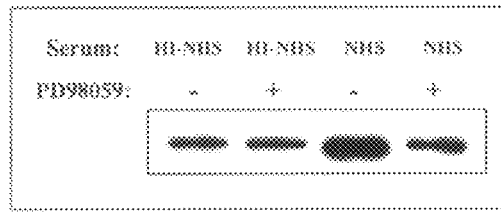
Figure 6B:
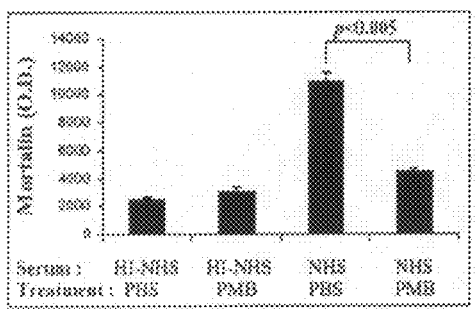
Figure 6D:
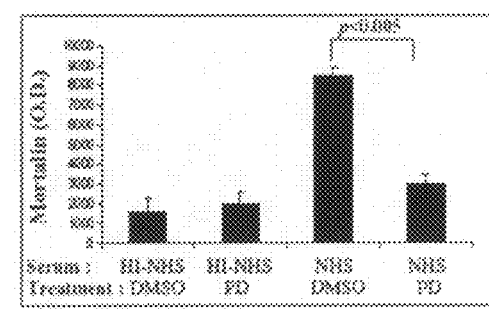
Figure 6E:
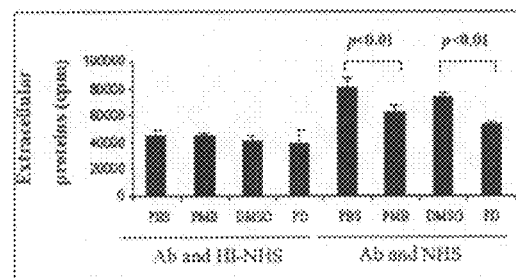
Figure 6F:
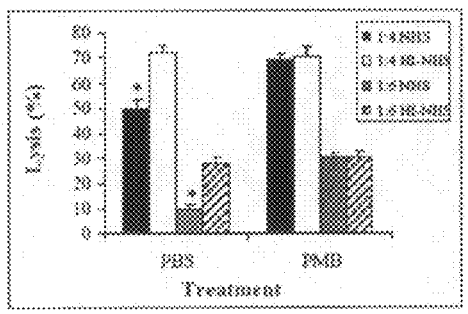
Figure 6G:
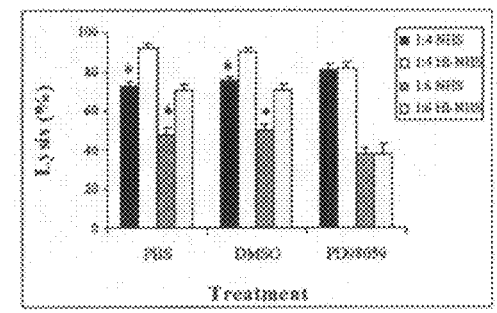

Involvement of PKC and ERK in mortalin release: Both PKC and ERK are known to contribute to cell resistance to complement damage (Kraus, S. and Fishelson, Z. 2000. Eur J Immunol 30:1272; Kraus, S. et al., 2001. Clin Exp Immunol 123:366). The effect of two PKC inhibitors, polymyxin B (PMB) and GF109203X, and of a MEK inhibitor, PD98059, on mortalin release was examined. Both PMB (FIGS. 6a-b) and PD98059 (FIGS. 6c-d) significantly reduced release of mortalin from complement-treated cells. A similar effect was observed with cells treated with another PKC inhibitor, GF109203X (not shown). PMB and PD98059 treatments also blocked the complement-induced release of metabolically-labeled proteins (FIG. 6e). To show a correlation between the effect of the PKC and MEK inhibitors on mortalin release and their effect on cell resistance to complement, the complement-induced protection assay was used (Carney, D. F. et al., 1985. J Immunol 134:1804). Cells were pre-treated with the inhibitors and then with a sublytic dose of antibody and complement. Next, the cells were treated with a lytic dose of antibody and complement. As shown in FIGS. 6f-g, cells pre-treated with sublytic complement and PBS or DMSO (solvent control to PD98059) acquired resistance to lytic complement doses. In contrast, cells pre-treated with sublytic complement and with PMB (FIG. 6f) or PD98059 (FIG. 6g) did not acquire the resistance to lytic complement.

Mortalin binds to complement C9 or to complement C8: To investigate the possibility that mortalin binds to the complement C9 protein, a protein-protein binding assay was performed, as previously described (Deng, J. et al., 2003. Infect Immun 71:6402). Human C9 was subjected to SDS-PAGE and transferred to a nitrocellulose membrane. The membrane was incubated with cell lysate, as a source for mortalin, and then with anti-mortalin antibody. Alternatively, the membrane was incubated with cell lysate pre-mixed with C9. As shown in FIG. 7, mortalin bound to blotted C9 and not to BSA. This binding could be competed with soluble C9, indicating that mortalin can bind to native epitopes on C9.

Similar results were obtained by enzyme-linked immunosorbent assay (ELISA; data not shown). Mortalin could bind to human C9 (and to a lower extend to human C8) attached to microtiter plates.

Figure 10A:
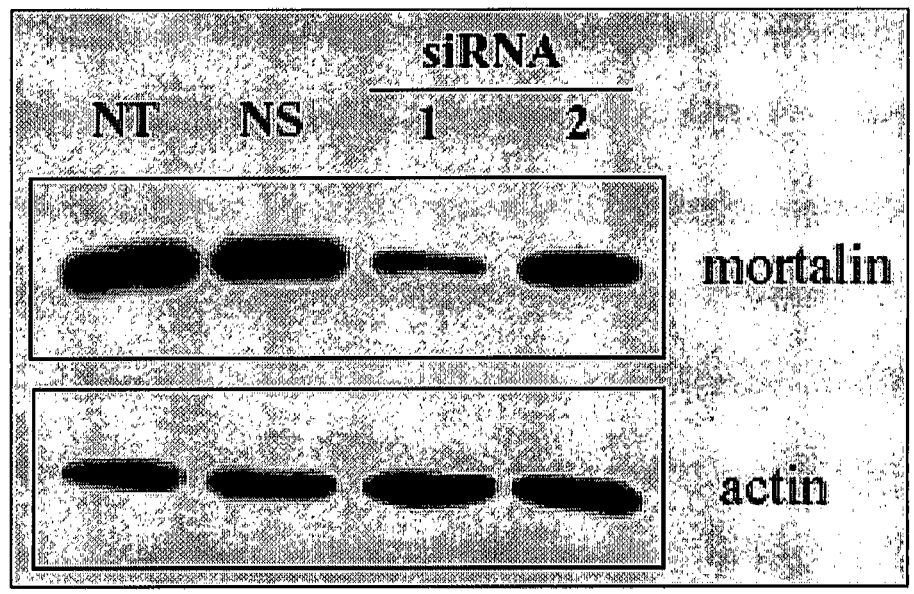
FIGS. 10a-b are Western immunoblotting and cell lysis assay data depicting that downregulation of mortalin by siRNA enhances cell sensitivity to complement. K562 cells (15,000 cells per milliliter) were transfected with 200 nanomolar siRNA1 or siRNA2 (SEQ. ID. NO. 12), both specific sequences of mortalin. Cells transfected with non-specific siRNA control (NS) or not treated at all (NT) were used as controls. At a time point 48 hours following transfection, cells were analyzed by SDS-PAGE and Western blotting using anti-mortalin and anti-actin antibodies (FIG. 10a). At the same time, transfected cells (4 million cells per milliliter) were treated with anti-K562 antibodies diluted 1:100 and with HI-NHS or NHS. Lysis was measured following 60 minutes incubation at 37 degrees centigrade (FIG. 10b). Results are representative of 2 independent experiments. Statistical analysis indicated a significant (*, p <0.005) difference between the cells transfected with the non-specific control and the cells transfected with the two types of siRNA.
Figure 10B:
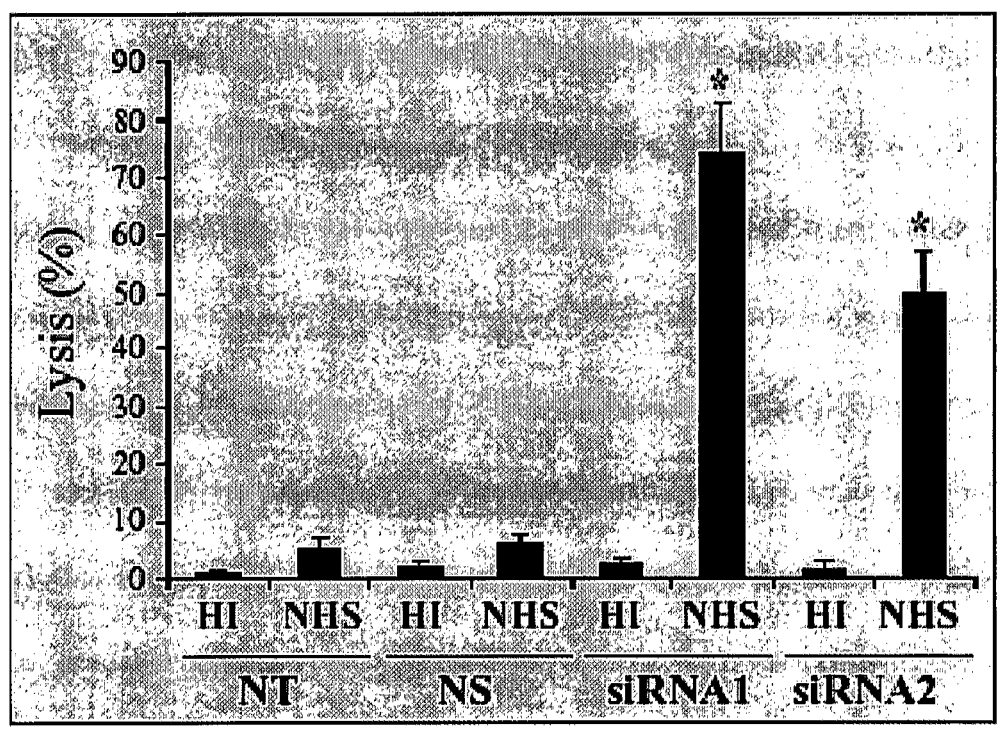

Up- and down-regulation of mortalin expression and its effect on complement lysis: Treatment with cathepsin L inhibitor leads to elevation of mortalin expression in K562 cells (FIG. 8a). This was accompanied by enhanced resistance of treated cells to lysis by antibody and complement (FIG. 8b). The level of expression of mortalin in K562 cells was also enhanced by transfection with pGFPC1-mortalin plasmid. As shown in FIG. 9, K562 transfectants bearing pGFPC1-mortalin were significantly more resistant to lysis by complement relative to K562 bearing an empty pGFPC1 vector and to untreated K562 cells. Next, the effect of small RNA interference on mortalin expression and on cell lysis was examined. Transfection of K562 cells with mortalin siRNA (two different sequences) caused a decrease in the level of expression of mortalin (FIG. 10a). Importantly, K562 cells transfected with mortalin-specific siRNAs were found to be more sensitive to killing by antibody and complement (FIG. 10b).

Discussion: The presently disclosed experimental results demonstrate that sublytic complement attack induces shedding of mortalin associated with membrane vesicles. This requires the complete assembly of the C5b-9 membrane attack complex, as heat-inactivation of complement or the absence of complement C7 or C8, preclude release of mortalin. The presently disclosed data also show that shedding of mortalin in response to complement attack is PKC- and ERK-dependent and occurs from viable cells. In support to the present claim that the extracellular mortalin originates from viable cells and not from damaged cells, it is shown that a similar level of sublytic damage caused by two other pore-formers, SLO and mellitin, does not induce release of mortalin.

The present discovery that anti-mortalin antibodies reduce mortalin secretion and increase cell sensitivity to complement-mediated lysis, suggests that shedding of mortalin is translated into resistance to complement, due to its function in acceleration of complement MAC elimination by membrane vesiculation. This is supported by the findings that:

1. Treatment with cathepsin L inhibitor enhanced mortalin expression and reduced cell lysis by complement;
2. Transfection with pGFPC1-mortalin plasmid led to mortalin over-expression and lowered cell killing by complement, and
3. Transfection with siRNA specific to mortalin silenced mortalin expression and sensitized the cells to lysis by complement.

Mortalin, also known as GRP75, PBP74, mitochondrial hsp75 and mot-2, is a member of the hsp70 family (GeneCard #GC05M137967). This protein has been assigned multiple functions including stress response, glucose regulation, p53 inactivation, control of cell proliferation, differentiation, tumorigenesis and mitochondrial import (reviewed in Wadhwa, R. et al., 2002. Cell Stress Chaperones 7:309). Mortalin is ubiquitously and constitutively expressed in normal tissues, and its expression level is upregulated in some tumors (Takano, S. et al., 1997. Exp Cell Res 237:38; Dundas, S R. et al., 2004. J Pathol 205:74) and during infection and inflammation (Kirmanoglou, K. et al., 2004. Basic Res Cardiol 99:404; Johannesen, J. et al., 2004. Is mortalin a candidate gene for T1DM ? Autoimmunity 37:423). Furthermore, overexpression of mortalin in normal cells considerably extends their lifespan (Kaul, S. C. et al., 2003. Exp Cell Res 286:96), while reduction of mortalin levels in immortalized cells causes growth arrest (Wadhwa, R. et al., 2004. J Gene Med 6:439). Thus far, mortalin has been mainly described inside cells, in mitochondria and several other cytoplasmic locations (Ran, Q. et al., 2000. Biochem Biophys Res Commun 275:174). It is presently disclosed that in unstimulated K562 cells, a diffused distribution pattern of mortalin in the cytoplasm that partly shifted was seen, following sublytic complement attack, to the cell periphery (data not shown). This occurred concomitantly with the shedding of mortalin from the cells. By flow cytometry analysis, mortalin was previously detected on the surface of mouse B-cells and macrophages (VanBuskirk, A. M. et al., 1991. J Immunol 146:500). In addition, profiling of cell surface proteome of biotinylated cancer cells, identified mortalin on neuroblastoma, lung adenocarcinoma, leukemia and ovarian cancer cells (Shin, B. K. et al., 2003. J Biol Chem 278:7607). Surprisingly, in the presently disclosed experiments, analysis by flow cytometry failed to detect mortalin on the surface of control and complement-triggered K562 cells (not shown). This may appear contradictory to the fact that following complement attack mortalin was found outside K562 cells associated with membrane vesicles and that anti-mortalin antibodies block shedding of mortalin. The presently disclosed data shows that the shedding process is very fast and within 5 minutes following a sublytic MAC attack, more than 50 percent of the total releasable mortalin is already in the supernatant. It is, therefore, conceivable that the amount of mortalin in transit on the cell surface is too small for detection by flow cytometry, and that its identification on or within the plasma membrane will require a more sensitive technique.

Elimination of MAC from Ehrlich ascites tumor cells was shown to be dependent on Ca2+ influx and PKC activity (Carney, D. F. et al., 1990. J Immunol 145:623). Both PKC and ERK contribute to cell protection from complement-mediated lysis (Kraus, S. and Fishelson, Z. 2000. Eur J Immunol 30:1272; Kraus, S. et al., 2001. Clin Exp Immunol 123: 366; Cybulsky, A. V. et al., 1990. Kidney Int 38:803) and as shown here, also to mortalin release. It is likely that the activation of PKC and ERK, following MAC-induced Ca2+ influx, mobilizes mortalin to the cell surface. This is followed, somehow, by sorting of MAC complexes and membrane vesiculation. Hsc70, another member of the hsp70 family, also migrates, in response to sublytic MAC, from the cytoplasm to the plasma membrane (Fishelson, Z. et al., 2001. Int Immunol 13:983). Both mortalin and hsc70 have an N-terminal ATPase domain and a C-terminal peptide binding domain (Krimmer, T. et al., 2000. Mol Cell Biol 20:5879; Flaherty, K. M. et al., 1990. Nature 346:623; Demand, J. et al., 1998. Mol Cell Biol 18:2023). Possibly, mortalin and hsc70 regulate or compose the machinery that uses ATP to force vesicle formation (budding) at the extracellular surface. Both mortalin and hsc70 bind to numerous other proteins, probably via their peptide binding domain. For example, mortalin was shown to bind to GRP94 (Takano, S. et al., 2001. Biochem J 357:393), p53 (Wadhwa, R. et al., 1998. J Biol Chem 273:29586), and FGF-1 (Mizukoshi, E. et al., 1999. Biochem J 343 Pt 2:461). An ATP-sensitive association between mortalin and IL-1 receptor type 1, that was independent on IL-1 binding, was also described (Sacht, G. et al., 1999. Biofactors 9:49). This raises the possibility that mortalin functions both in internalization and externalization of proteins. Within the cell, mortalin plays a major role in import of proteins into mitochondria (Voisine, C. et al., 1999. Cell 97:565). The presently disclosed finding of a possible mortalin-C9 binding (FIG. 7) indicates that on the surface of MAC-attacked cells, mortalin recognizes the complement membrane attack complexes via C9 and contributes to the gathering of these complexes to specific vesiculation sites. This is supported by the observation that SLO and mellitin do not induce release of mortalin.

Spontaneous shedding of membrane vesicles has been extensively documented with many types of normal and malignant cells. These vesicles, named exosomes or prostasomes, are apparently secreted by exocytosis as a consequence of fusion of multivesicular late endosome/lysosome bodies (MVB) with the plasma membrane (Fevrier, B. and Raposo, G. 2004. Curr Opin Cell Biol 16:415; Llorente, A. et al., 2004. J Cell Sci 117:5343; Ronquist, G. and Brody, 1. 1985. Biochim Biophys Acta 822:203). Prostasomes are released by prostate normal epithelial cells and carcinoma cells and are found in semen (Ronquist, G. and Brody, 1. 1985. Biochim Biophys Acta 822:203). As both exosomes and prostasomes are enriched in raft molecules, both are found intracellularly in MVB and their release is sensitive to wortmannin, prostasomes could actually represent specific exosomes of the prostate tissue (Llorente, A. et al., 2004. J Cell Sci 117:5343). High cholesterol content was found in exosomes (Wubbolts, R. et al., 2003. J Biol Chem 278:10963), prostasomes (Arvidson, G. et al., 1989. Biochim Biophys Acta 984:167) and in MAC-containing membrane vesicles (Stein, J. M. and Luzio, J. P. 1991. Biochem J 274 (Pt 2):381). Nevertheless, at present, it seems improbable that the MAC/mortalin containing membrane vesicles are exosomes-like. It is not likely that the large MAC complexes are endocytosed, transported to the late endosomal compartment, packed into MVB and gets exocytosed within 5-10 minutes. Transferrin receptors reach the recycling endosome only after approximately 20 minutes (Sheff, D. et al., 2002. J Cell Biol 156:797; Hao, M. and Maxfield, F. R. 2000. J Biol Chem 275:15279). In addition, extracellular application of anti-mortalin antibodies blocked the MAC-induced vesiculation process, suggesting that the process occurs on the cell surface. Extensive proteomic profiling has been performed on exosomes derived from human B-cells (Wubbolts, R. et al., 2003. J Biol Chem 278:10963), mesothelioma cells (Hegmans, J. P. et al., 2004. Am J Pathol 164:1807), melanoma cells (Mears, R. et al., 2004. Proteomics 4:4019) and on prostasomes (Utleg, A. G. et al., 2003. Prostate 56:150). Mortalin was not identified in those studies and not in K562 cells-derived exosomes (Savina, A. et al., 2003. J Biol Chem 278:20083; de Gassart, A. et al., 2003. Blood 102:4336). In contrast, hsc70 was detected in exosomes (Wubbolts, R. et al., 2003. J Biol Chem 278:10963; Mears, R. et al., 2004. Proteomics 4:4019; Thery, C. et al., 2001. J Immunol 166:7309) and in prostasomes (Utleg, A. G. et al., 2003. Prostate 56:150). These data suggest that the MAC/mortalin vesicles are generated differently from exosomes or that mortalin is attracted specifically to MAC-induced membrane vesicles. Theoretically, the simplest way to shed MAC/mortalin membrane vesicles is by a direct budding-off from the plasma membrane or by sloughing of membrane blebs. Alternatively, a novel mode of endocytosis may be proposed, involving formation of a double membrane endosome or formation of an MVB at the cell periphery, followed by an immediate exocytosis via an early endosomal compartment. This is required for release of membrane vesicles following the fusion of the early endosome with the plasma membrane. The reported $t_{1/2}$ of recycling of transferrin receptors and lipids via the early endosomal compartment ranges between 1.4 to 6 minutes (Sheff, D. et al., 2002. J Cell Biol 156:797; Hao, M. and Maxfield, F. R. 2000. J Biol Chem 275:15279), which fits well with the observed rate of MAC/mortalin release. It is also possible that sublytic complement induces an accelerated rate of MAC endocytosis and recycling via the recycling endosome/perinuclear MVB compartment. Electron microscopy studies performed on neutrophils activated with sublytic complement (Morgan, B. P. et al., 1987. J Immunol 138:246) or with FMLP (Hess, C. et al., 1999. J Immunol 163:4564) demonstrated direct budding of membrane vesicles (named ectosomes) from the surface of the neutrophils. Direct membrane vesiculation was also described with human erythrocytes under MAC attack (Iida, K. et al., 1991. J Immunol 147: 2638). Elucidation of the mechanism of MAC/mortalin release from K562 and other cells on membrane vesicles requires further investigation.

Mortalin can bind intact proteins and peptides, and may associate with peptides that are cryptic in intact proteins. Thus, mortalin (PBP74) was demonstrated to bind to a peptide fragment of pigeon cytochrome c, but not to the same region in native cytochrome c (Vanbuskirk, A. et al., 1989. J Exp Med 170:1799). The peptide dissociated from mortalin upon binding of ATP to mortalin. Based on this study it was suggested that mortalin plays a role in antigen presentation. More recently, mortalin (GRP75) was implicated in presentation of a tumor specific antigen to cytotoxic T lymphocytes (CTL) expressing TCR-gamma-delta (Kim, H. T. et al., 1995. J Immunol 154:1614). That antibodies directed to mortalin, blocked cytolysis of Burkitt's lymphoma cells by gamma-delta CTL, suggested that mortalin presented the tumor antigen at the cell surface. Other members of the hsp70 family and related chaperones are known to be involved in peptide binding and antigen presentation and are considered as novel agents for immunotherapy of cancer and infection (Castelli, C. et al., 2004. Cancer Immunol Immunother 53:227; Srivastava, P. 2002. Annu Rev Immunol 20:395). Exosomes derived from dendritic or cancer cells are also being considered for cancer immunotherapy (Fevrier, B. and Raposo, G. 2004. Curr Opin Cell Biol 16:415; Chaput, N. et al., 2004. Cancer Immunol Immunother 53:234). Such exosomes express MHC-peptide complexes that can be targeted to antigen-presenting cells, thus amplifying specific immune responses (Van Niel, G. et al., 2003. Gut 52:1690). Given that membrane vesicles released following sublytic complement attack may contain mortalin-peptide/protein complexes and that mortalin is capable of presenting antigens to T cells, it is intriguing to propose that, like MHC-loaded exosomes, mortalin-loaded membrane vesicles may express immunomodulatory effects in normal and pathological immune responses. Mortalin over-expression in cancer has been correlated with poor patient survival (Dundas, S. R. et al., 2004. J Pathol 205:74), and, under certain conditions, exosomes can suppress anti-tumor immune responses (Taylor, D. D. and Gercel-Taylor, C. 2005. Br J Cancer; Riteau, B. et al., 2003. Hum Immunol 64:1064).

Thus, assembly of a sublytic dose of the complement membrane attack complex on K562 cells is followed by a rapid release of the MAC on membrane vesicles. The presently disclosed data indicates that mortalin becomes integrated into these membrane vesicles and is involved in the process of vesiculation. Elimination of the MAC is a protective mechanism from complement-mediated lysis. Cells subjected to sublytic MAC become, within 20-50 minutes, more resistant to lytic MAC doses (Reiter, Y. et al., 1992. Eur J Immunol 22:1207). This could be, at least partly, due to translocation of mortalin to the cell cortex, thus permitting elimination of the second wave MAC at an accelerated rate. It is predicted that this process occurs also in-vivo and that MAC/mortalin-bearing membrane vesicles occur in patients at sites of immune autoreactivity, inflammation and transplantation and in tumors subjected to immunotherapy. Release of MAC-loaded vesicles from endothelial cells was proposed to contribute to fibrin deposition associated with immune endothelial injury (Hamilton, K. K. et al., 1990. J Biol Chem 265:3809).

Summary: The membrane attack complex (MAC) of the complement system causes membrane damage and cell death. For protection, cells have adopted several resistance mechanisms, including removal of membrane inserted MAC by vesiculation. In the presently described experiments, to identify proteins involved in MAC vesiculation, extracellular proteins released from a human cancer cell line in response to treatment with sublytic complement were separated by acrylamide gel electrophoresis and protein bands were extracted, digested into peptides and the peptides were analyzed by mass spectrometry. A 75 kDa protein that was abundant in supernatant of complement-treated cells, was identified as mortalin/GRP75. Analysis by Western blotting demonstrated that as early as five minutes following exposure to sublytic doses of complement, mortalin was released from the cancer cells. Mortalin release required a fully active complement system and was dependent on assembly of the C5b-9 complex. Other pore-formers, such as streptolysin 0 and mellitin, did not induce release of mortalin. Apparently, mortalin was shed in vesicles containing also complement C9. Four types of presently disclosed experiments demonstrated that targeting of mortalin can affect complement-mediated cytotoxicity:

1. Co-treatment of complement-treated cancer cells with anti-mortalin antibodies reduced mortalin release from the cells and sensitized the cells to complement-mediated cytolysis.

2. Treatment of cancer cells with cathepsin L inhibitor enhanced mortalin expression and reduced complement-mediated cytolysis.

3. Cancer cells transfected to overexpress mortalin were protected from complement-mediated cytolysis.

4. Transfection of cancer cells with siRNA specific to mortalin silenced mortalin expression and sensitized the cells to lysis by complement. Inhibitors of PKC and ERK also prevented mortalin release from complement-activated cells.

Conclusion: It is presently taught for the first time that increasing mortalin levels/activity can be used to effectively protect cells from complement-mediated cytotoxicity, and hence can be used to effectively treat diseases associated with pathological complement-mediated cytotoxicity, such as autoimmune, immune complex and transplantation-related diseases. It is further presently taught for the first time that decreasing mortalin activity/levels, can be used to effectively sensitize pathological cells, such as cancer cells, to complement-mediated cytotoxicity, and hence to effectively treat via such cytotoxicity diseases associated with such cells, such as tumoral, infectious, autoimmune and transplantation-related diseases. As such, the presently disclosed method of regulating of mortalin activity/levels to treat disease overcomes the limitations of the prior art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications and sequences identified by their GenBank accession numbers mentioned in this specification are herein incorporated in their entirety by reference into the specification, to the same extent as if each individual publication, patent, or patent application or sequence identified by its GenBank accession number was specifically and individually indicated to be incorporated herein by reference. In addition, citation or identification of any reference in this application shall not be construed as an admission that such reference is available as prior art to the present invention.

REFERENCES CITED

Additional References are Cited in the Text

Arvidson, G., Ronquist, G., Wikander, G., and Ojteg, A. C. 1989. Human prostasome membranes exhibit very high cholesterol/phospholipid ratios yielding high molecular ordering. Biochim Biophys Acta 984:167.

Bhakdi, S., Tranum-Jensen, J., and Sziegoleit, A. 1985. Mechanism of membrane damage by streptolysin-O. Infect Immun 47:52.

Bohana-Kashtan, O., Ziporen, L., Donin, N., Kraus, S., and Fishelson, Z. 2004. Cell signals transduced by complement. Mol Immunol 41:583.

Carette, J., Lehnert, S., and Chow, T. Y. 2002. Implication of PBP74/mortalin/GRP75 in the radio-adaptive response. Int J Radiat Biol 78:183.

Carney, D. F., Koski, C. L., and Shin, M. L. 1985. Elimination of terminal complement intermediates from the plasma membrane of nucleated cells: the rate of disappearance differs for cells carrying C5b-7 or C5b-8 or a mixture of C5b-8 with a limited number of C5b-9. J Immunol 134:1804.

Carney, D. F., Lang, T. J., and Shin, M. L. 1990. Multiple signal messengers generated by terminal complement complexes and their role in terminal complement complex elimination. J Immunol 145:623.

Castelli, C., Rivoltini, L., Rini, F., Belli, F., Testori, A., Maio, M., Mazzaferro, V., Coppa, J., Srivastava, P. K., and Parmiani, G. 2004. Heat shock proteins: biological functions and clinical application as personalized vaccines for human cancer. Cancer Immunol Immunother 53:227.

Chaput, N., Taieb, J., Schartz, N. E., Andre, F., Angevin, E., and Zitvogel, L. 2004. Exosome-based immunotherapy. Cancer Immunol Immunother 53:234.

Cragg, M. S., Howatt, W. J., Bloodworth, L., Anderson, V. A., Morgan, B. P., and Glennie, M. J. 2000. Complement mediated cell death is associated with DNA fragmentation. Cell Death Differ 7:48.

Cybulsky, A. V., Bonventre, J. V., Quigg, R. J., Lieberthal, W., and Salant, D. J. 1990. Cytosolic calcium and protein kinase C reduce complement-mediated glomerular epithelial injury. Kidney Int 38:803.

Dashiell, S. M., Rus, H., and Koski, C. L. 2000. Terminal complement complexes concomitantly stimulate proliferation and rescue of Schwann cells from apoptosis. Glia 30:187.

de Gassart, A., Geminard, C., Fevrier, B., Raposo, G., and Vidal, M. 2003. Lipid raft-associated protein sorting in exosomes. Blood 102:4336.

Demand, J., Luders, J., and Hohfeld, J. 1998. The carboxy-terminal domain of Hsc7O provides binding sites for a distinct set of chaperone cofactors. Mol Cell Biol 18:2023.

Deng, J., Gold, D., LoVerde, P. T., and Fishelson, Z. 2003. Inhibition of the complement membrane attack complex by Schistosoma mansoni paramyosin. Infect Immun 71:6402.

Dundas, S. R., Lawrie, L. C., Rooney, P. H., and Murray, G. 1. 2004. Mortalin is over-expressed by colorectal adenocarcinomas and correlates with poor survival. J Pathol 205:74.

Fevrier, B. and Raposo, G. 2004. Exosomes: endosomal-derived vesicles shipping extracellular messages. Curr Opin Cell Biol 16:415.

Fishelson, Z., Hochman, I., Greene, L. E., and Eisenberg, E. 2001. Contribution of heat shock proteins to cell protection from complement-mediated lysis. Int Immunol 13:983.

Flaherty, K. M., DeLuca-Flaherty, C., and McKay, D. B. 1990. Three-dimensional structure of the ATPase fragment of a 70K heat-shock cognate protein. Nature 346:623.

Hamilton, K. K., Hattori, R., Esmon, C. T., and Sims, P. J. 1990. Complement proteins C5b-9 induce vesiculation of the endothelial plasma membrane and expose catalytic surface for assembly of the prothrombinase enzyme complex. J Biol Chem 265:3809.

Hao, M. and Maxfield, F. R. 2000. Characterization of rapid membrane internalization and recycling. J Biol Chem 275:15279.

Hess, C., Sadallah, S., Hefti, A., Landmann, R., and Schifferli, J. A. 1999. Ectosomes released by human neutrophils are specialized functional units. J Immunol 163:4564.

Johannesen, J., Pie, A., Karlsen, A. E., Larsen, Z. M., Jensen, A., Vissing, H., Kristiansen, O. P., Pociot, F., and Nerup, J. 2004. Is mortalin a candidate gene for T1DM ? Autoimmunity 37:423.

Hegmans, J. P., Bard, M. P., Hemmes, A., Luider, T. M., Kleijmeer, M. J., Prins, J. B., Zitvogel, L., Burgers, S. A., Hoogsteden, H. C., and Lambrecht, B. N. 2004. Proteomic analysis of exosomes secreted by human mesothelioma cells. Am J Pathol 164:1807.

Iida, K., Whitlow, M. B., and Nussenzweig, V. 1991. Membrane vesiculation protects erythrocytes from destruction by complement. J Immunol 147:2638.

Kaul, S. C., Yaguchi, T., Taira, K., Reddel, R. R., and Wadhwa, R. 2003. Overexpressed mortalin (mot-2)/mthsp70/GRP75 and hTERT cooperate to extend the in-vitro lifespan of human fibroblasts. Exp Cell Res 286:96.

Kim, H. T., Nelson, E. L., Clayberger, C., Sanjanwala, M., Sklar, J., and Krensky, A. M. 1995. Gamma delta T cell recognition of tumor Ig peptide. J Immunol 154:1614.

Kirmanoglou, K., Hannekum, A., and Schafler, A. E. 2004. Expression of mortalin in patients with chronic atrial fibrillation. Basic Res Cardiol 99:404.

Koski, C. L., Ramm, L. E., Hammer, C. H., Mayer, M. M., and Shin, M. L. 1983. Cytolysis of nucleated cells by complement: cell death displays multi-hit characteristics. Proc Natl Acad Sci U S A 80:3816.

Kraus, S. and Fishelson, Z. 2000. Cell desensitization by sublytic C5b-9 complexes and calcium ionophores depends on activation of protein kinase C. Eur J Immunol 30:1272.

Kraus, S., Seger, R., and Fishelson, Z. 2001. Involvement of the ERK mitogen-activated protein kinase in cell resistance to complement-mediated lysis. Clin Exp Immunol 123:366.

Krimmer, T., Rassow, J., Kunau, W. H., Voos, W., and Pfanner, N. 2000. Mitochondrial protein import motor: the ATPase domain of matrix Hsp7O is crucial for binding to Tim44, while the peptide binding domain and the carboxy-terminal segment play a stimulatory role. Mol Cell Biol 20:5879.

Laine, R. O., Morgan, B. P., and Esser, A. F. 1988. Comparison between complement and melittin hemolysis: antimelittin antibodies inhibit complement lysis. Biochemistry 27:5308.

Llorente, A., de Marco, M. C., and Alonso, M. A. 2004. Caveolin-1 and MAL are located on prostasomes secreted by the prostate cancer PC-3 cell line. J Cell Sci 117:5343.

Mears, R., Craven, R. A., Hanrahan, S., Totty, N., Upton, C., Young, S. L., Patel, P., Selby, P. J., and Banks, R. E. 2004. Proteomic analysis of melanoma-derived exosomes by two-dimensional polyacrylamide gel electrophoresis and mass spectrometry. Proteomics 4:4019.

Merrick, B. A., Walker, V. R., He, C., Patterson, R. M., and Selkirk, J. K. 1997. Induction of novel Grp75 isoforms by 2-deoxyglucose in human and murine fibroblasts. Cancer Lett 119:185.

Mizukoshi, E., Suzuki, M., Loupatov, A., Uruno, T., Hayashi, H., Misono, T., Kaul, S. C., Wadhwa, R., and Imamura, T. 1999. Fibroblast growth factor-1 interacts with the glucose-regulated protein GRP75/mortalin. Biochem J 343 Pt 2:461.

Morgan, B. P. 1992. Effects of the membrane attack complex of complement on nucleated cells. Curr Top Microbiol Immunol 178:115. Morgan, B. P., Dankert, J. R., and Esser, A. F. 1987. Recovery of human neutrophils from complement attack: removal of the membrane attack complex by endocytosis and exocytosis. J Immunol 138:246.

Morgan, B. P., Imagawa, D. K., Dankert, J. R., and Ramm, L. E. 1986. Complement lysis of U937, a nucleated mammalian cell line in the absence of C9: effect of C9 on C5b-8 mediated cell lysis. J Immunol 136:3402.

Muller-Eberhard, H. J. 1986. The membrane attack complex of complement. Annu Rev Immunol 4:503.

Ran, Q., Wadhwa, R., Kawai, R., Kaul, S. C., Sifers, R. N., Bick, R. J., Smith, J. R., and Pereira-Smith, O. M. 2000. Extramitochondrial localization of mortalin/mthsp70/PBP74/GRP75. Biochem Biophys Res Commun 275:174.

Reiter, Y., Ciobotariu, A., and Fishelson, Z. 1992. Sublytic complement attack protects tumor cells from lytic doses of antibody and complement. Eur J Immunol 22:1207.

Reiter, Y., Ciobotariu, A., Jones, J., Morgan, B. P., and Fishelson, Z. 1995. Complement membrane attack complex, perforin, and bacterial exotoxins induce in K562 cells calcium-dependent cross-protection from lysis. J Immunol 155:2203.

Reiter, Y. and Fishelson, Z. 1992. Complement membrane attack complexes induce in human leukemic cells rapid expression of large proteins (L-CIP). Mol Immunol 29:771.

Riteau, B., Faure, F., Menier, C., Viel, S., Carosella, E. D., Amigorena, S., and Rouas-Freiss, N. 2003. Exosomes bearing HLA-G are released by melanoma cells. Hum Immunol 64:1064.

Ronquist, G. and Brody, I. 1985. The prostasome: its secretion and function in man. Biochim Biophys Acta 822:203.

Sacht, G., Brigelius-Flohe, R., Kiess, M., Sztajer, H., and Flohe, L. 1999. ATP-sensitive association of mortalin with the IL-1 receptor type I. Biofactors 9:49.

Savina, A., Furlan, M., Vidal, M., and Colombo, M. I. 2003. Exosome release is regulated by a calcium-dependent mechanism in K562 cells. J Biol Chem 278:20083.

Sheff, D., Pelletier, L., O'Connell, C. B., Warren, G., and Mellman, I. 2002. Transferrin receptor recycling in the absence of perinuclear recycling endosomes. J Cell Biol 156:797.

Scolding, N. J., Morgan, B. P., Houston, W. A., Linington, C., Campbell, A. K., and Compston, D. A. 1989. Vesicular removal by oligodendrocytes of membrane attack complexes formed by activated complement. Nature 339:620.

Shin, B. K., Wang, H., Yim, A. M., Le Naour, F., Brichory, F., Jang, J. H., Zhao, R., Puravs, E., Tra, J., Michael, C. W., Misek, D. E., and Hanash, S. M. 2003. Global profiling of the cell surface proteome of cancer cells uncovers an abundance of proteins with chaperone function. J Biol Chem 278:7607.

Sims, P. J. and Wiedmer, T. 1986. Repolarization of the membrane potential of blood platelets after complement damage: evidence for a Ca++-dependent exocytotic elimination of C5b-9 pores. Blood 68:556.

Srivastava, P. 2002. Interaction of heat shock proteins with peptides and antigen presenting cells: chaperoning of the innate and adaptive immune responses. Annu Rev Immunol 20:395.

Stein, J. M. and Luzio, J. P. 1991. Ectocytosis caused by sublytic autologous complement attack on human neutrophils. The sorting of endogenous plasma-membrane proteins and lipids into shed vesicles. Biochem J 274 (Pt 2):381.

Takano, S., Wadhwa, R., Mitsui, Y., and Kaul, S. C. 2001. Identification and characterization of molecular interactions between glucose-regulated proteins (GRPs) mortalin/GRP75/peptide-binding protein 74 (PBP74) and GRP94. Biochem J 357:393.

Takano, S., Wadhwa, R., Yoshii, Y., Nose, T., Kaul, S. C., and Mitsui, Y. 1997. Elevated levels of mortalin expression in human brain tumors. Exp Cell Res 237:38.

Taylor, D. D. and Gercel-Taylor, C. 2005. Tumour-derived exosomes and their role in cancer-associated T-cell signalling defects. Br J Cancer.

Thery, C., Boussac, M., Veron, P., Ricciardi-Castagnoli, P., Raposo, G., Garin, J., and Amigorena, S. 2001. Proteomic analysis of dendritic cell-derived exosomes: a secreted subcellular compartment distinct from apoptotic vesicles. J Immunol 166:7309.

Utleg, A. G., Yi, E. C., Xie, T., Shannon, P., White, J. T., Goodlett, D. R., Hood, L., and Lin, B. 2003. Proteomic analysis of human prostasomes. Prostate 56:150.

Van Niel, G., Mallegol, J., Bevilacqua, C., Candalh, C., Brugiere, S., Tomaskovic-Crook, E., Heath, J. K., Cerf-Bensussan, N., and Heyman, M. 2003. Intestinal epithelial exosomes carry MHC class II/peptides able to inform the immune system in mice. Gut 52:1690.

Vanbuskirk, A., Crump, B. L., Margoliash, E., and Pierce, S. K. 1989. A peptide binding protein having a role in antigen presentation is a member of the HSP70 heat shock family. J Exp Med 170:1799.

VanBuskirk, A. M., DeNagel, D. C., Guagliardi, L. E., Brodsky, F. M., and Pierce, S. K. 1991. Cellular and subcellular distribution of PBP72/74, a peptide-binding protein that plays a role in antigen processing. J Immunol 146:500.

Voisine, C., Craig, E. A., Zufall, N., von Ahsen, O., Pfanner, N., and Voos, W. 1999. The protein import motor of mitochondria: unfolding and trapping of preproteins are distinct and separable functions of matrix Hsp70. Cell 97:565.

Wadhwa, R., Kaul, S. C., Ikawa, Y., and Sugimoto, Y. 1993. Identification of a novel member of mouse hsp70 family. Its association with cellular mortal phenotype. J Biol Chem 268:6615.

Wadhwa, R., Taira, K., and Kaul, S. C. 2002. An Hsp70 family chaperone, mortalin/mthsp70/PBP74/Grp75: what, when, and where? Cell Stress Chaperones 7:309.

Wadhwa, R., Takano, S., Robert, M., Yoshida, A., Nomura, H., Reddel, R. R., Mitsui, Y., and Kaul, S. C. 1998. Inactivation of tumor suppressor p53 by mot-2, a hsp70 family member. J Biol Chem 273:29586.

Wadhwa, R., Takano, S., Taira, K., and Kaul, S. C. 2004. Reduction in mortalin level by its antisense expression causes senescence-like growth arrest in human immortalized cells. J Gene Med 6:439.

Wadhwa, R., Yaguchi, T., Hasan, M. K., Mitsui, Y., Reddel, R. R., and Kaul, S. C. 2002. Hsp70 family member, mot-2/mthsp70/GRP75, binds to the cytoplasmic sequestration domain of the p53 protein. Exp Cell Res 274:246.

Walport, M. J. 2001. Complement. First of two parts. N Engl J Med 344:1058.

Wubbolts, R., Leckie, R. S., Veenhuizen, P. T., Schwarzmann, G., Mobius, W., Hoemschemeyer, J., Slot, J. W., Geuze, H. J., and Stoorvogel, W. 2003. Proteomic and biochemical analyses of human B cell-derived exosomes. Potential implications for their function and multivesicular body formation. J Biol Chem 278:10963.

SEQUENCE LISTING

<160> NUMBER OF SEQ ID NOS: 10

<210> SEQ ID NO 1
<211> LENGTH: 679
<212> TYPE: PRT
<213> ORGANISM: Homo sapiens

<400> SEQUENCE: 1

```
Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285

Glu Phe Lys Arg Glu Thr Gly Val Asp Leu Thr Lys Asp Asn Met Ala
    290                 295                 300

Leu Gln Arg Val Arg Glu Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
        355                 360                 365
```

```
Ala Met Gln Asp Ala Glu Val Ser Lys Ser Asp Ile Gly Glu Val Ile
        370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
        435                 440                 445

Thr Leu Gly Gly Val Phe Thr Lys Leu Ile Asn Arg Asn Thr Thr Ile
        450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
        515                 520                 525

Ile Val His Val Ser Ala Lys Asp Lys Gly Thr Gly Arg Glu Gln Gln
        530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Asp Arg Arg Lys Lys
                565                 570                 575

Glu Arg Val Glu Ala Val Asn Met Ala Glu Gly Ile Ile His Asp Thr
                580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
        610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675

<210> SEQ ID NO 2
<211> LENGTH: 679
<212> TYPE: PRT
<213> ORGANISM: Homo sapiens

<400> SEQUENCE: 2

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45

Glu Ala Ile Lys Gly Ala Val Val Gly Ile Asp Leu Gly Thr Thr Asn
    50                  55                  60
```

```
Ser Cys Val Ala Val Met Glu Gly Lys Gln Ala Lys Val Leu Glu Asn
 65                  70                  75                  80

Ala Glu Gly Ala Arg Thr Thr Pro Ser Val Ala Phe Thr Ala Asp
             85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
            115                 120                 125

Asp Asp Pro Glu Val Gln Lys Asp Ile Lys Asn Val Pro Phe Lys Ile
            130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
            195                 200                 205

Gly Gln Ile Ser Gly Leu Asn Val Leu Arg Val Ile Asn Glu Pro Thr
            210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
            275                 280                 285

Glu Phe Lys Arg Glu Thr Gly Val Asp Leu Thr Lys Asp Asn Met Ala
290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
            405                 410                 415

Val Ala Ile Gly Ala Ala Ile Gln Gly Gly Val Leu Ala Gly Asp Val
            420                 425                 430

Thr Asp Val Leu Leu Asp Val Thr Pro Leu Ser Leu Gly Ile Glu
            435                 440                 445

Thr Leu Gly Gly Val Phe Thr Lys Leu Ile Asn Arg Asn Thr Thr Ile
450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
```

|  |  | 485 |  |  | 490 |  |  | 495 |  |  |  |
|---|---|---|---|---|---|---|---|---|---|---|---|

Asn Lys Leu Leu Gly Gln Phe Thr Leu Ile Gly Ile Pro Pro Ala Pro
          500               505            510

Arg Gly Val Pro Gln Ile Glu Val Thr Phe Asp Ile Asp Ala Asn Gly
     515            520            525

Ile Val His Val Ser Ala Lys Asp Lys Gly Thr Gly Arg Glu Gln Gln
 530              535           540

Ile Val Ile Gln Ser Ser Gly Gly Leu Ser Lys Asp Asp Ile Glu Asn
545             550            555           560

Met Val Lys Asn Ala Glu Lys Tyr Ala Glu Glu Asp Arg Arg Lys Lys
          565             570            575

Glu Arg Val Glu Ala Val Asn Met Ala Glu Gly Ile Ile His Asp Thr
     580            585            590

Glu Thr Lys Met Glu Glu Phe Lys Asp Gln Leu Pro Ala Asp Glu Cys
 595              600           605

Asn Lys Leu Lys Glu Glu Ile Ser Lys Met Arg Glu Leu Leu Ala Arg
610             615            620

Lys Asp Ser Glu Thr Gly Glu Asn Ile Arg Gln Ala Ala Ser Ser Leu
625             630            635           640

Gln Gln Ala Ser Leu Lys Leu Phe Glu Met Ala Tyr Lys Lys Met Ala
          645             650            655

Ser Glu Arg Glu Gly Ser Gly Ser Ser Gly Thr Gly Glu Gln Lys Glu
     660            665            670

Asp Gln Lys Glu Glu Lys Gln
 675

<210> SEQ ID NO 3
<211> LENGTH: 681
<212> TYPE: PRT
<213> ORGANISM: Homo sapiens

<400> SEQUENCE: 3

Gly Thr Val Ile Ser Ala Ser Arg Ala Ala Ala Ala Arg Leu Val Gly
1              5              10            15

Ala Ala Ala Ser Arg Gly Pro Thr Ala Ala Arg His Gln Asp Ser Trp
          20             25            30

Asn Gly Leu Ser His Glu Ala Phe Arg Leu Val Ser Arg Arg Asp Tyr
      35             40            45

Ala Ser Glu Ala Ile Lys Gly Ala Val Val Gly Ile Asp Leu Gly Thr
 50              55           60

Thr Asn Ser Cys Val Ala Val Met Glu Gly Lys Arg Ala Lys Val Leu
65             70            75           80

Glu Asn Ala Glu Gly Ala Arg Thr Thr Pro Ser Val Val Ala Phe Thr
          85             90            95

Ala Asp Gly Glu Arg Leu Val Gly Met Pro Ala Lys Arg Gln Ala Val
          100            105          110

Thr Asn Pro Asn Asn Thr Phe Tyr Ala Thr Lys Arg Leu Ile Gly Arg
     115            120           125

Arg Tyr Asp Asp Pro Glu Val Gln Lys Asp Ile Lys Asn Val Pro Phe
 130              135           140

Lys Ile Val Arg Ala Ser Asn Gly Asp Ala Trp Val Glu Ala His Gly
145             150            155           160

Lys Leu Tyr Ser Pro Ser Gln Ile Gly Ala Phe Val Leu Met Lys Met
          165            170          175

Lys Glu Thr Ala Glu Asn Tyr Leu Gly Arg Thr Ala Lys Asn Ala Val

```
                    180                 185                 190
Ile Thr Val Pro Ala Tyr Phe Asn Asp Ser Gln Arg Gln Ala Thr Lys
            195                 200                 205

Asp Ala Gly Gln Ile Ser Gly Leu Asn Val Leu Arg Val Ile Asn Glu
210                 215                 220

Pro Thr Ala Ala Ala Leu Ala Tyr Gly Leu Asp Lys Ser Glu Asp Lys
225                 230                 235                 240

Val Ile Ala Val Tyr Asp Leu Gly Gly Gly Thr Phe Asp Ile Ser Ile
            245                 250                 255

Leu Glu Ile Gln Lys Gly Val Phe Glu Val Lys Ser Thr Asn Gly Asp
                260                 265                 270

Thr Phe Leu Gly Gly Glu Asp Phe Asp Gln Ala Leu Leu Arg His Ile
        275                 280                 285

Val Lys Glu Phe Lys Arg Glu Thr Gly Val Asp Leu Thr Lys Asp Asn
    290                 295                 300

Met Ala Leu Gln Arg Val Arg Glu Ala Ala Glu Lys Ala Lys Cys Glu
305                 310                 315                 320

Leu Ser Ser Ser Val Gln Thr Asp Ile Asn Leu Pro Tyr Leu Thr Met
                325                 330                 335

Asp Ser Ser Gly Pro Lys His Leu Asn Met Lys Leu Thr Arg Ala Gln
            340                 345                 350

Phe Glu Gly Ile Val Thr Asp Leu Ile Arg Arg Thr Ile Ala Pro Cys
        355                 360                 365

Gln Lys Ala Met Gln Asp Ala Glu Val Ser Lys Ser Asp Ile Gly Glu
    370                 375                 380

Val Ile Leu Val Gly Gly Met Thr Arg Met Pro Lys Val Gln Gln Thr
385                 390                 395                 400

Val Gln Asp Leu Phe Gly Arg Ala Pro Ser Lys Ala Val Asn Pro Asp
                405                 410                 415

Glu Ala Val Ala Ile Gly Ala Ala Ile Gln Gly Gly Val Leu Ala Gly
            420                 425                 430

Asp Val Thr Asp Val Leu Leu Leu Asp Val Thr Pro Leu Ser Leu Gly
        435                 440                 445

Ile Glu Thr Leu Gly Gly Val Phe Thr Lys Leu Ile Asn Arg Asn Thr
    450                 455                 460

Thr Ile Pro Thr Lys Lys Ser Gln Val Phe Ser Thr Ala Ala Asp Gly
465                 470                 475                 480

Gln Thr Gln Val Glu Ile Lys Val Cys Gln Gly Glu Arg Glu Met Ala
                485                 490                 495

Gly Asp Asn Lys Leu Leu Gly Gln Phe Thr Leu Ile Gly Ile Pro Pro
            500                 505                 510

Ala Pro Arg Gly Val Pro Gln Ile Glu Val Thr Phe Asp Ile Asp Ala
        515                 520                 525

Asn Gly Ile Val His Val Ser Ala Lys Asp Lys Gly Thr Gly Arg Glu
    530                 535                 540

Gln Gln Ile Val Ile Gln Ser Ser Gly Gly Leu Ser Lys Asp Asp Ile
545                 550                 555                 560

Glu Asn Met Val Lys Asn Ala Glu Lys Tyr Ala Glu Glu Asp Arg Arg
                565                 570                 575

Lys Lys Glu Arg Val Glu Ala Val Asn Met Ala Glu Gly Ile Ile His
            580                 585                 590

Asp Thr Glu Thr Lys Met Glu Glu Phe Lys Asp Gln Leu Pro Ala Asp
        595                 600                 605
```

```
Glu Cys Asn Lys Leu Lys Glu Glu Ile Ser Lys Met Arg Glu Leu Leu
        610                 615                 620

Ala Arg Lys Asp Ser Glu Thr Gly Glu Asn Ile Arg Gln Ala Ala Ser
625                 630                 635                 640

Ser Leu Gln Gln Ala Ser Leu Lys Leu Phe Glu Met Ala Tyr Lys Lys
                645                 650                 655

Met Ala Ser Glu Arg Glu Gly Ser Gly Ser Ser Gly Thr Gly Glu Gln
                660                 665                 670

Lys Glu Asp Gln Lys Glu Glu Lys Gln
            675                 680

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

Asp Ala Gly Gln Ile Ser Gly Leu Asn Val Leu Arg
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Val Gln Gln Thr Val Gln Asp Leu Phe Gly Arg
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic peptide

<400> SEQUENCE: 6

Gln Ala Val Thr Asn Pro Asn Asn Thr Phe Tyr Ala Thr Lys
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic peptide

<400> SEQUENCE: 7

Asn Ala Val Ile Thr Val Pro Ala Tyr Phe Asn Asp Ser Gln Arg
1               5                   10                  15

<210> SEQ ID NO 8
<211> LENGTH: 13
<212> TYPE: PRT
<213> ORGANISM: Artificial sequence
<220> FEATURE:
<223> OTHER INFORMATION: Synthetic peptide

<400> SEQUENCE: 8

Asp Ile Gly Glu Val Ile Leu Val Gly Gly Met Thr Arg
1               5                   10
```

```
<210> SEQ ID NO 9
<211> LENGTH: 15
<212> TYPE: PRT
<213> ORGANISM: Artificial sequence
<220> FEATURE:
<223> OTHER INFORMATION: Synthetic peptide

<400> SEQUENCE: 9

Thr Phe Asp Ile Ser Ile Leu Glu Ile Gln Lys Gly Val Phe Glu
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: Synthetic peptide

<400> SEQUENCE: 10

Gln Thr Gln Val Glu Ile Lys Val Cys Gln Gly Glu Arg Glu
1               5                   10

<
```

What is claimed is:

1. A method of decreasing vesicular shedding of complement from cancer cells and increasing complement-mediated cytolysis of cancer cells, thereby augmenting the cytolytic effect of antibodies that bind to cancer cells and recruit complement thereto, wherein the cancer cells are lymphoma/leukemia cells, colorectal cancer cells or bladder cancer cells, comprising:
  administering to the cancer cells antibodies that specifically bind the cancer cells and include a moiety capable of initiating complement-mediated cytotoxicity, and
  decreasing the level of a polypeptide of SEQ ID NO:1 (mortalin) in cancer cells by administering to the cancer cells a mortalin-specific siRNA molecule, which is capable of decreasing the level of expression of mortalin in the cancer cells, wherein the mortalin-specific siRNA molecule is administered in an amount effective to decrease the level of expression of said mortalin by an amount sufficient to decrease vesicular shedding of complement from cancer cells and increase complement-mediated cytolysis of cancer cells, thereby augmenting the cytolytic effect of said antibodies.

2. The method in accordance with claim 1, wherein said moiety capable of initiating complement-mediated cytotoxicity is an antibody constant region.

3. The method in accordance with claim 1, wherein said cancer cells are leukemia cells.

4. The method in accordance with claim 1, wherein the cancer cells to which the antibodies and siRNA are administered are of a type against which the therapeutic effectiveness of the antibodies and the siRNA has been established in vitro.

* * * * *